United States Patent
Britto et al.

(10) Patent No.: US 11,834,698 B2
(45) Date of Patent: Dec. 5, 2023

(54) PROCESS FOR DETERMINING ENZYME ACTIVITY IN A CELL BY ACTIVITY-BASED REPORTER GENE TECHNOLOGY (ABRGT)

(71) Applicant: INDIAN INSTITUTE OF SCIENCE EDUCATION AND RESEARCH, Pune (IN)

(72) Inventors: Sandanaraj Selvaraj Britto, Pune (IN); Punita Bathla, Pune (IN)

(73) Assignee: INDIAN INSTITUTE OF SCIENCE EDUCATION AND RESEARCH, Pune (IN)

( * ) Notice: Subject to any disclaimer, the term of this patent is extended or adjusted under 35 U.S.C. 154(b) by 674 days.

(21) Appl. No.: 16/401,906

(22) Filed: May 2, 2019

(65) Prior Publication Data
US 2019/0338373 A1 Nov. 7, 2019

(30) Foreign Application Priority Data

May 2, 2018 (IN) .............................. 201821016607

(51) Int. Cl.
*C12Q 1/37* (2006.01)
*G01N 33/542* (2006.01)
(Continued)

(52) U.S. Cl.
CPC ............. *C12Q 1/37* (2013.01); *C12N 9/6472* (2013.01); *G01N 33/5005* (2013.01);
(Continued)

(58) Field of Classification Search
CPC .... C12Q 1/37; C12N 9/6472; G01N 33/5005; G01N 33/542; G01N 2333/96466;
(Continued)

(56) References Cited

U.S. PATENT DOCUMENTS

2003/0175986 A1 9/2003 Patricelli
2010/0233726 A1 9/2010 Tsien et al.

FOREIGN PATENT DOCUMENTS

WO 97/11094 A2 3/1997
WO 2012/118715 A9 9/2012

OTHER PUBLICATIONS

Bedner et al. (Experimental Cell Research, vol. 259, pp. 308-313; 2000). (Year: 2000).*

(Continued)

*Primary Examiner* — Allison M Fox
*Assistant Examiner* — Qing Xu
(74) *Attorney, Agent, or Firm* — DeLizio, Peacock, Lewin & Guerra, LLP

(57) ABSTRACT

Methods and materials for specific imaging of active enzyme in a live or intact cell are disclosed. The enzyme of interest tagged to reporter protein (donor) is exogenously expressed in a cell. The conversion of proenzyme to active enzyme (containing reporter protein) is achieved upon applying an appropriate stimulus to the target cells. The activated enzyme is labelled with an activity-based probe carrying a fluorophore (acceptor). The covalent labelling of active enzyme by the activity-based probe creates a FRET pair which provides the opportunity to exquisitely image the function of an "active enzyme". This method is used for specific imaging of the function of active caspase-3,-7,-8,-9 and cathepsin-B and also for profiling of inhibitors of caspases and cathepsin B.

Figure 1:
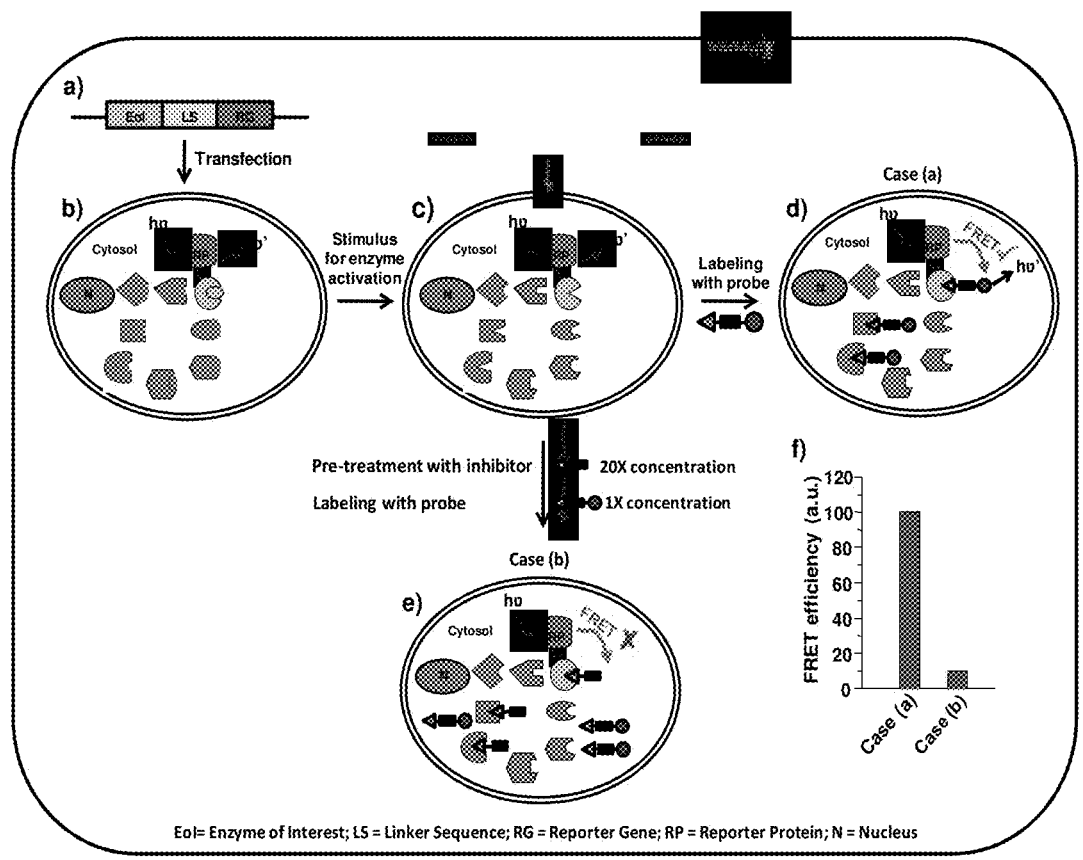

13 Claims, 19 Drawing Sheets
(18 of 19 Drawing Sheet(s) Filed in Color)

(51) Int. Cl.
*C12N 9/64* (2006.01)
*G01N 33/50* (2006.01)

(52) U.S. Cl.
CPC .... *G01N 33/542* (2013.01); *C12Y 304/22001* (2013.01); *C12Y 304/2206* (2013.01); *C12Y 304/22056* (2013.01); *C12Y 304/22061* (2013.01); *C12Y 304/22062* (2013.01); *G01N 2333/96466* (2013.01)

(58) Field of Classification Search
CPC .... C12Y 304/22001; C12Y 304/22056; C12Y 304/2206; C12Y 304/22061; C12Y 304/22062
See application file for complete search history.

(56) References Cited

OTHER PUBLICATIONS

Jones et al. (Journal of Biomolecular Screening, vol. 5, No. 5, pp. 307-317; 2000). (Year: 2000).*
Mpakou et al. (Development, Growth and Differentiation, vol. 48, pp. 419-428; 2006). (Year: 2006).*
Martinez-Castillo et al., PLOS one, vol. 11, No. 11; e0165971; pp. 1-18 (2016) (Year: 2016).*
Bastiaens, et al., "Microspectroscopic imaging tracks the intracellular processing of a signal transduction protein: Fluorescent-labeled protein kinase C (31", Proc. Natl. Acad. Sci. USA, vol. 93, pp. 8407-8412. (Aug. 1996).
Bertrand, et al., "Induction of a Common Patrhway of Apoptosis by Staurosporine", Experimental Cell Research, 211, pp. 314-321. (1994).
Chalfie, et al., "Green Fluorescent Protein as a Marker for Gene Expression", Science, vol. 263, pp. 802-805. (Feb. 11, 1994).
Edgington, et al., "Noninvasive optical imaging of apoptosis by caspase-targeted activity-based probes", Nature Medicine, vol. 15, No. 8, pp. 967-947. (Aug. 2009).
Micale, et al., "Design and Synthesis of a Potent and Selective Peptidomimetic Inhibitor of Caspase-3", J. Med. Chem., 47, pp. 6455-6458. (2004).
Siegel, et al., "Measurement of Molecular Interactions in Living Cells by Fluorescence Resonance Energy Transfer Between Variants of the Green Fluorescent Protein", Science's stke (http://www.stke.org/cgi/content/full/OC_sigtrans;2000/38/pl1), 7 pages. (Downloaded Nov. 15, 2015).
Stennicke, et al., "Caspases: Preparation and Characterization", Methods: A company to Methods in Enzymology 17, pp. 313-319. (1999).
Weissleder, et al., "Imaging in the era of molecular oncology", Nature, vol. 452, pp. 580-589. (Apr. 3, 2008).
Wiley, et al., "Identification and Characterization of a New Member of the TNF Family that Induces Apoptosis", Immunity, vol. 3, pp. 673-682. (Dec. 1995).
Zhivotovsky, et al., "Caspases: their intracellular localization and translocation during apoptosis", Cell Death and Differentiation, 6, pp. 644-651. (1999).
Pratt, et al. "Direct Measurement of Cathespin B Activity in the Cytosol of Apoptotic Cells by an Activity-Based Probe", Chemisty & Biology, 16, pp. 1001-1012. (Sep. 25, 2009).

* cited by examiner

PROCESS FOR DETERMINING ENZYME ACTIVITY IN A CELL BY ACTIVITY-BASED REPORTER GENE TECHNOLOGY (ABRGT)

TECHNICAL FIELD OF THE INVENTION

The present invention relates to a process for determining enzyme activity in a cell by activity-based reporter gene technology (AbRGT).

The present invention provides the AbRGT employs fluorescence resonance energy transfer (FRET)-based readout to measure the "active-state" of an enzyme. The enzyme activity measurements are performed in a live cell with absolute specificity by the present invention.

BACKGROUND AND PRIOR ART OF THE INVENTION

Majorly, enzymes are synthesized by ribosomes as zymogens, i.e., inactive enzymes which undergo post-translational modification (PTM) to become active enzymes. An example of PTM is the cleaving of peptide bonds or the processing of the pro-peptide (zymogen) to form a fully functional mature enzyme, i.e., an active enzyme. The transition from the zymogen to an active enzyme is tightly regulated. Alterations in regulation of enzyme activity can lead to severe pathological conditions including cancer, auto-immune disorders such as arthritis and neurodegenerative disorders, etc. Therefore, understanding the activation status of enzymes with high specificity will aid in understanding the pathological processes and would help in developing novel drug targets.

In the past few decades, immense efforts have been undertaken by researchers to monitor enzyme activity. A review article titled 'Imaging in the era of molecular oncology' by Weissleder et al. in *Nature reviews* (2008) focuses on the power of optical molecular imaging tools to non-invasively study the complexity and in vivo behavior of cancers. The utility of imaging tools such as fluorescence imaging, non-fluorescent based optical imaging and labelling methods such as genetic reporters and exogenous cell trackers in locating tumors have been discussed therein.

Discovery of the green fluorescent protein (GFP) from jellyfish *Aequorea victoria* by Nobel Laureates, Osamu Shimomura, Martin Chalfie and Roger Tsien, elevated imaging science to the next level. An article named 'Green fluorescent protein as a marker for gene expression' published in Science (1994) by the Martin Chalfie describes a method that demonstrates the use of GFP in determining the expression level and localization of enzyme of interest by tagging it to GFP.

PCT Publication No. WO1997/011094 further discloses spectral variants of GFP. These variants were synthesized by site-directed mutagenesis of key residues of GFP; Ser65, Tyr66, and Gly67 which cyclizes to the phenolate form, resulting in chromophore formation. Certain point mutations resulted in better fluorescence signals and photo-stability than wild type GFPS. Other point mutations led to the discovery of color mutants of GFP that excites and emits at a different wavelength than GFP. These variants were named as cyan fluorescent protein (CFP), yellow fluorescent protein (YFP), blue fluorescent protein (BFP), red fluorescent protein (RFP), etc. The breakthrough of the discovery of GFP color variants allowed the simultaneous monitoring of the expression of more than one gene in the cells.

Further, an article titled 'Measurement of molecular interactions in living cells by fluorescence resonance energy transfer between variants of the green fluorescent protein' published by Roger Tsien's laboratory in Science (2000) unfolds the utility of GFP spectral variants in FRET phenomenon. FRET phenomenon requires the use of two fluorophores, in which one acts as a fluorescence energy donor and other acts as a fluorescence energy acceptor, kept within close proximity, e.g., within 10 nm of each other. It also necessitates a significant spectral overlap between the donor and the acceptor fluorophore. These features of the FRET phenomenon allowed its manipulation in the biological system in monitoring protein-protein interactions.

US Patent Publication No. 2010/0233726 discloses an approach which exploits the FRET phenomenon exhibited by fluorescent reporter proteins (FRPs) in determining the activity of an enzyme both in vitro and in vivo. A plasmid construct comprising sequences encoding two FRPs that makes up a FRET pair has been used therein. It consists of a donor and an acceptor FRP coupled via a peptide linker whose recognition and cleavage moiety mimics the binding site of a true substrate. Cleavage by the enzyme at the peptide linker results in FRET loss. The loss in the FRET effect acts as an indirect readout of the enzyme activity. In present times, this strategy of examining the enzyme activity is widely known as substrate-based reporter gene technology.

US Patent Publication No. 2003/0175986 discloses the use of another system of monitoring enzyme activity, called activity-based probe (ABP) technology. This tool employs a fluorescently labelled activity-based probe (fABP) to detect the presence of an active enzyme. The fABP shares three core structural elements: a reactive functional group called warhead, which reacts with the enzyme's active-site residue by covalently modifying it, a linker sequence that helps in recognition by a family of enzyme and a fluorescent reporter for identification. Since the reaction is based on a specific mechanism and involves the participation of active enzyme, the extent of active site modification serves as an indirect readout of activity levels in in vitro and in vivo systems.

PCT Publication No. WO2012/118715 discloses the development of quenched ABP (qABP) technology, a sub-family of ABP. The approach is similar to ABP probe with an added quencher molecule. The quencher molecule is attached to the reactive warhead group resulting in quenching of the fluorescence of the fluorophore by FRET phenomenon. The advantage of using qABP is that it only becomes fluorescent upon covalent modification of active enzyme, unlike fABP that emits fluorescence signal both when bound and unbound to the enzyme.

Current technologies can measure a class of active enzyme in the cell lysate samples, live cells and in vivo model systems with certain shortcomings. The major limitations of these prevalent tools involve the lack of substrate specificity and cross-reactivity. To date, no tool is available that can monitor the activity of one particular enzyme with exquisite specificity.

An article titled 'Non-invasive optical imaging of apoptosis by caspase-targeted activity-based probes' by Bogyo et al. published in *Nature Medicine* (2009) discloses efforts made by researchers to develop fABP to monitor the specific activation of caspases in apoptosis signalling pathway. A library of 50 compounds with (acyloxy) methyl ketone (AOMK) as a warhead based ABP was synthesized to screen for the ABP that would specifically react with caspase family and show minimal cross-reactivity with other cysteine proteases. To minimise the cross-reactivity, they changed the P2 residue of ABP to proline. Using the same strategy, they changed single residue in the ABP to track any change in reactivity. They shortlisted 4 compounds for further studies and were successful in reducing cross-reactivity to other proteases except for legumain. These studies indicate that it is nearly impossible to construct an ABP reactive to one particular enzyme with negligible cross-reactivity.

Considering the limitations of the available tools, the present invention unravels a strategy that is capable of detecting the activity of an enzyme with absolute specificity in living cells. Because of this specificity one does not have to engineer a small molecule probe to have very high specificity as long as the probe has a moderate affinity for the target enzyme. The present inventors have provided an invention that serves as an important application in understanding diseases and also to test the efficacy of targeted drugs.

SUMMARY OF THE INVENTION

In order to encounter the drawbacks of the prevalent techniques, the inventors of the present invention have provided a tool called AbRGT that can monitor the enzyme activity with exquisite specificity using the FRET effect. AbRGT is a fusion of the reporter gene technology and ABP technology.

In an aspect, the present invention provides a process for determining the activity of an enzyme in a cell by using AbRGT comprising;
a) preparing a cell overexpressing the enzyme of interest (EoI) tagged to a reporter protein acting as a fluorescence donor with an inducing agent,
b) introducing an fABP comprising a warhead, a linker sequence, and a fluorescent acceptor moiety into the cell,
c) allowing the fABP to covalently modify the EoI tagged to a reporter protein to form an in-situ FRET pair, and
d) measuring a fluorescence signal from the FRET pair.

Accordingly, the readout of this technology is based on the FRET effect, which is a very accurate, sensitive method and can be performed in a live cell with great resolution. The FRET occurrence is validated by the acceptor photobleaching method.

The scope of this tool is explored in to screen the activation of an enzyme in a biochemical pathway, testing the drug efficacy and also to study the dynamics of enzyme activation.

DETAILED DESCRIPTION OF DRAWINGS

The patent or application file contains at least one drawing executed in color. Copies of this patent or patent application publication with color drawing(s) will be provided by the Office upon request and payment of the necessary fee.

In order to better understand various exemplary embodiments, reference is made to the accompanying drawings, wherein:

FIG. 1 depicts a schematic representation of AbRGT. (a) Plasmid DNA encoding enzyme of interest (EoI) (yellow) tagged to a reporter gene (green). (b) Cell expressing EoI tagged to reporter enzyme along with other enzymes with the same or different enzyme family (grey). (c) Conversion of the active enzyme from inactive zymogen form upon application of an appropriate stimulus. (d) Case-a, EoI tagged to RP, labelled with FABP (1× concentration) showing FRET effect. (e) Case-b, cells are pre-treated with the active-site enzyme inhibitor (20× concentrations) and then labelled with FABP abolishes FRET effect. (f) Hypothetical graphical representation of FRET efficiency comparison between case (a) and (b).

Figure 2:
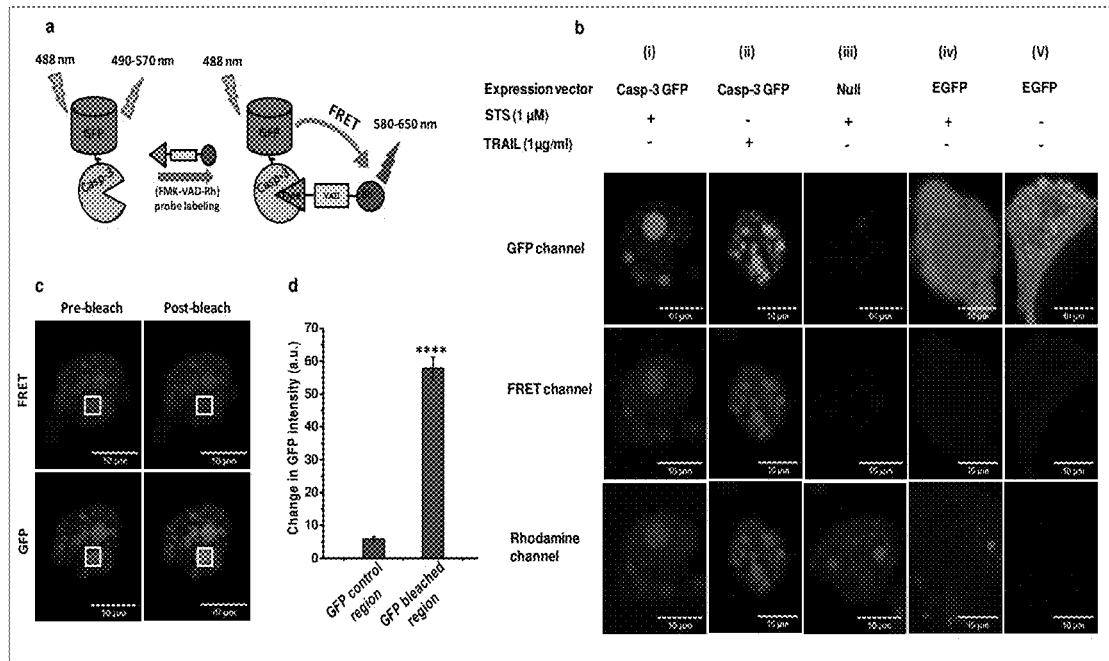

FIG. 2 depicts (a) a schematic representation of AbRGT in determining the specific activation of caspase-3 GFPspark tagged enzyme by FRET effect utilizing Rh-VAD-FMK (probe 1). (b) The fluorescence signal was collected in GFP, FRET and Rhodamine (Rh) channels. MCF-7 cells transfected with caspase-3 GFPspark treated with (i) 1 μM STS for 4 h or (ii) 1 μg/ml TRAIL for 5 h and then labelled with probe 1. (iii) Un-transfected MCF-7 cells were treated with 1 μM STS for 4 h and then labelled with the probe 1. MCF-7 cells transfected with enhanced green fluorescent protein (EGFP) plasmid treated (iv) with 1 μM STS or (v) without STS for 4 h and then labelled with probe 1, scale bar, 10 a.u. (c) FRET validation between GFPspark and rhodamine fluorophore using the acceptor photobleaching method. Images for GFP and rhodamine fluorescence signals were collected in GFP and FRET channels pre- and post-bleaching of rhodamine signals. (d) Quantification of change in GFP fluorescence intensity after rhodamine photo-bleaching in both unbleached control region and rhodamine bleached region, region of interest (ROI), area under the white square. Error bar represents the s.e.m for n=15 cells (*P<0.00001). Scale bar, 10 μm. a.u., arbitrary units.

Figure 3:
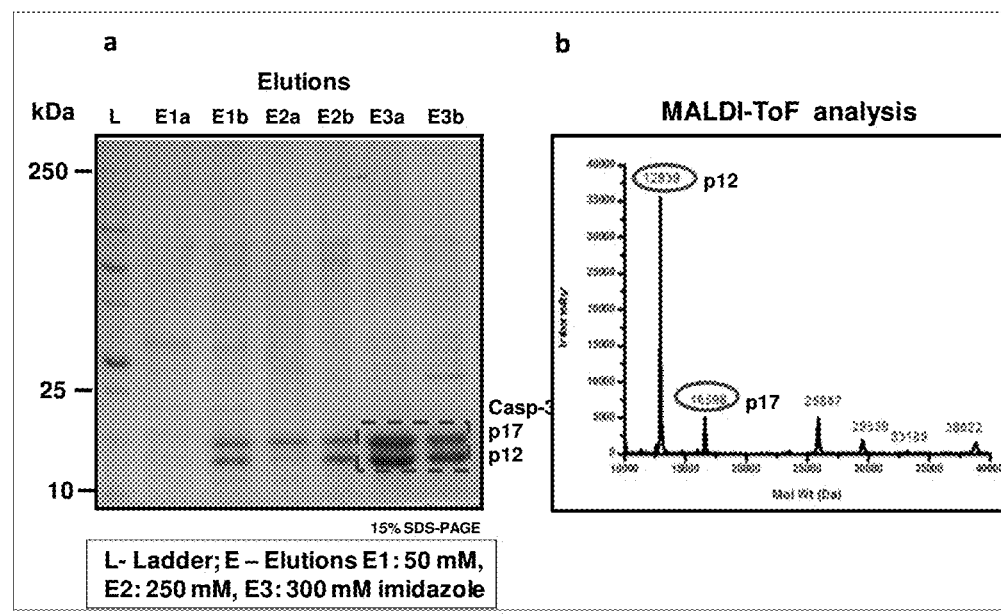

FIG. 3 depicts (a) SDS-PAGE analysis of Ni-NTA affinity column purified caspase-3. Enzyme samples were run on 15% SDS-PAGE gel and stained with Coomassie brilliant blue. Fractions were eluted with 50, 250 and 300 mM imidazole concentrations. (b) MALDI-ToF analysis of the purified recombinant caspase-3 (rcaspase-3). Caspase-3 was mixed with matrix (0.1% TFA with 70:30 water/acetonitrile mixtures) and the sample was loaded on the plate to get the accurate molecular weight in +1 and +2 states. The purified rcaspase-3 was confirmed with the two peaks obtained at 12939 and 16598 Da.

Figure 4:
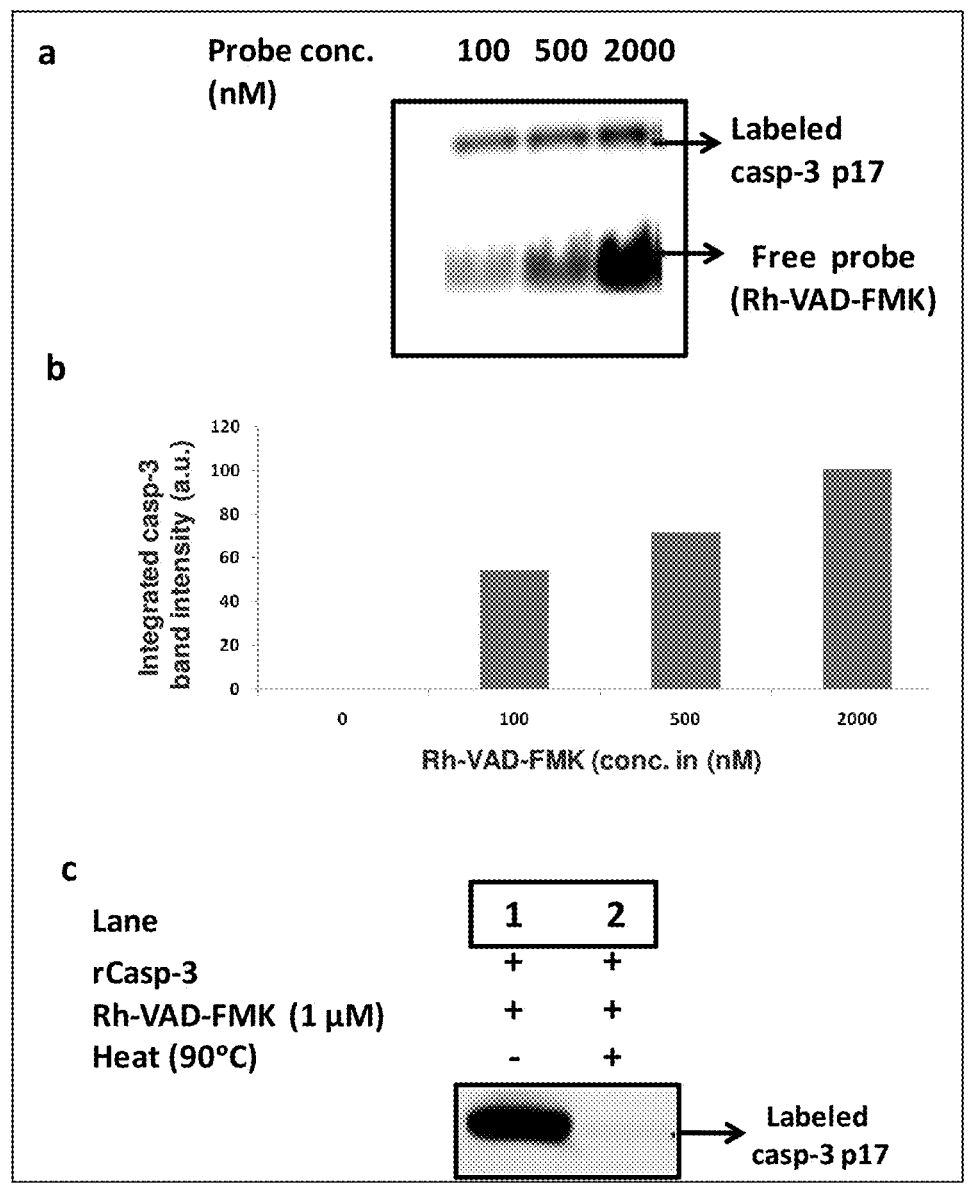

FIG. 4 depicts (a) labelling of purified rcaspase-3 (2 μM) by probe 1 at a concentration of 100, 500 and 2000 nM. (b) integrated band intensity values. (c) The specificity of probe 1 (1 μM) to label active enzyme (500 nM); (lane 1: active rcaspase-3 in the presence of probe 1, lane 2: thermally denatured rcaspase-3 in the presence of probe 1.

Figure 5:
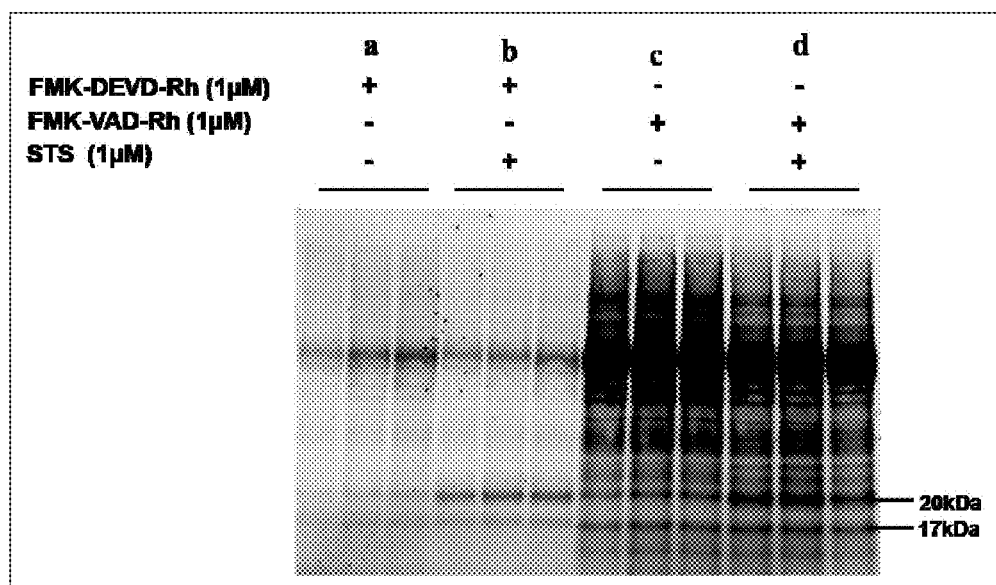

FIG. 5 depicts cellular off-target labelling of the probe 1 shown in Jurkat cells 2.5 million Jurkat cells were incubated with 1 μM probe 1 in the (b) presence or (c) the absence of STS (1 μM) for 6 h. Cells are incubated (a) without and (d) with the probe 1 and STS. Cells comprising labelled enzymes were lysed and analyzed by 12% SDS-PAGE followed by scanning for rhodamine fluorescence (Ex: 561 nm, Em: 605 nm) with a flat-bed laser scanner.

Figure 6A:
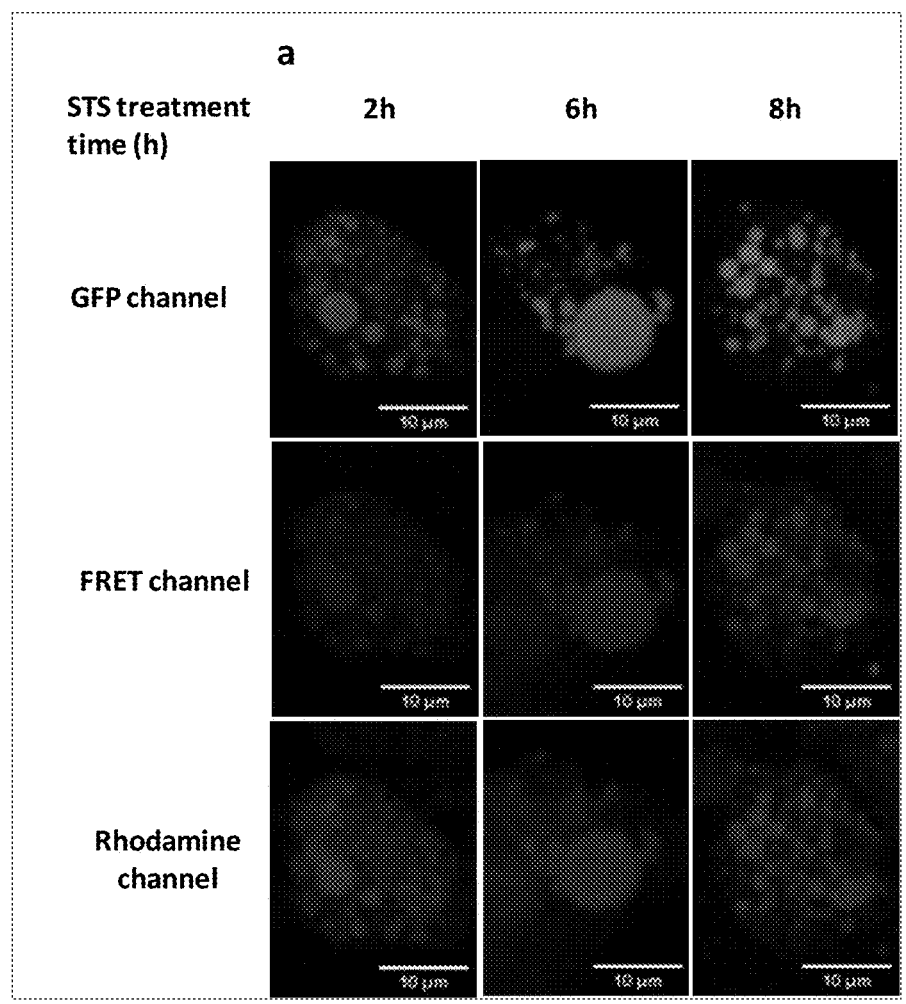
Figure 6B:
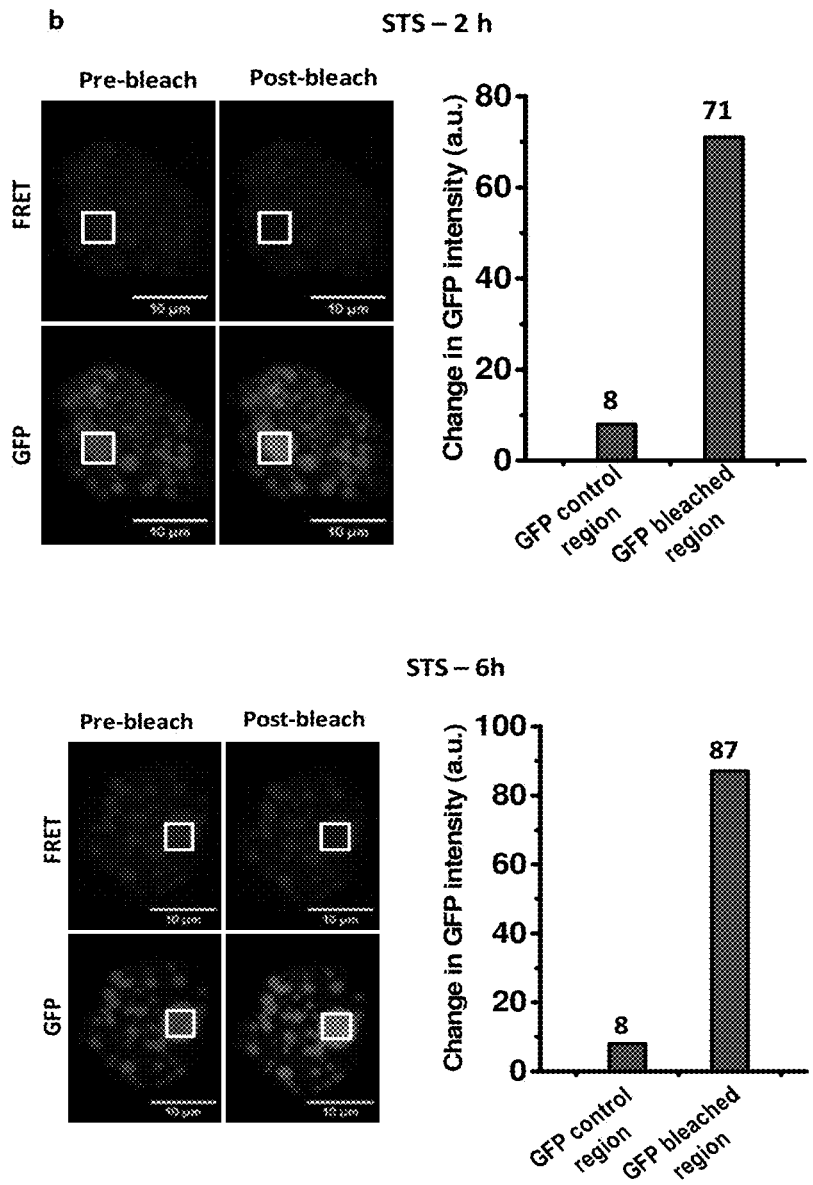

FIGS. 6A and 6B depict time dependent activation of caspase-3 GFPspark in MCF-7 cells upon STS (1 μM) induction. MCF-7 cells transfected with 2 μg of caspase-3 GFPspark plasmid and treated with 1 μM of STS for 2, 6, and 8 h. Cells were then labelled with the probe 1 for an additional 2 h. As seen in FIG. 6A, images were collected in GFP, FRET and Rh channel. As seen in FIG. 6B, images for GFP and rhodamine fluorescence signals were collected in GFP and FRET channels pre- and post-bleaching of rhodamine signals in ROI with 100% laser intensity (561 nm). FRET validation between GFPspark and rhodamine fluorophore using the acceptor photobleaching method for the MCF-7 cells with STS induction for 2, 6 and 8 h. I=intensity (a.u.), arbitrary units. The calculated FRET efficiency for 2, 6 and 8 h are 38, 43, and 36% respectively.

Figure 7A:
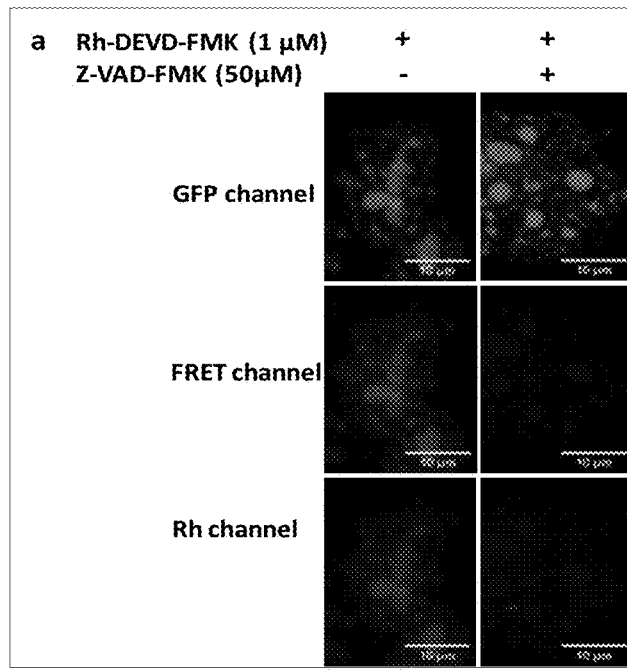
Figure 7B:
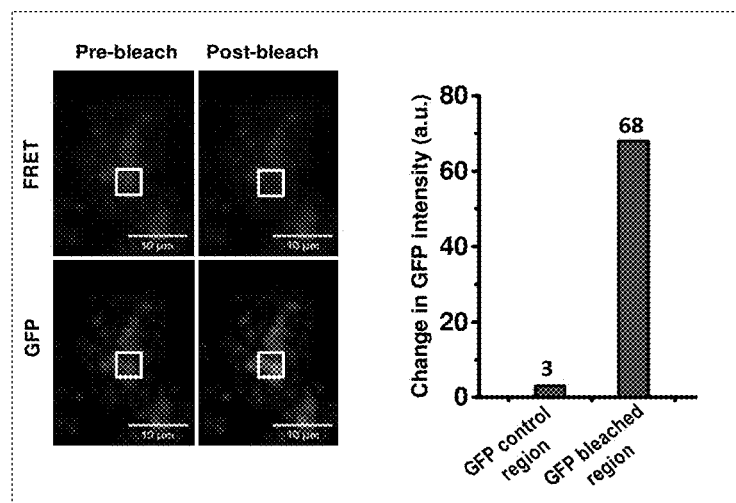

FIGS. 7A and 7B depict applying AbRGT for specific detection of active caspase-3 GFPspark using the Rh-DEVD-FMK (probe 2). Caspase-3 GFPspark (2 μg) overexpressing MCF-7 cells were treated with 1 μM of STS for 4 h and labelled with the probe 2 (1 μM). As seen in FIG. 7A, the fluorescence signal was collected in GFPspark, FRET and Rh channel in the presence and absence of inhibitor Z-VAD-FMK (50 μM). As seen in FIG. 7B, the acceptor photobleaching experiment was performed to confirm and calculate FRET efficiency. The rise in GFPspark intensity after rhodamine photobleaching in the background is insignificant as compared to the ROI, i.e., 68 a.u., with a calculated FRET efficiency of 35%.

Figures 8A, 8B:
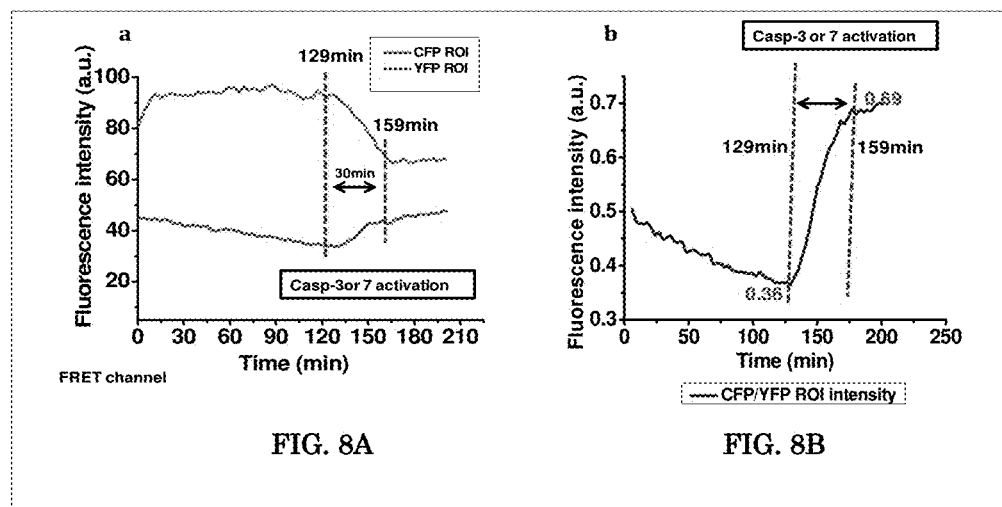

FIGS. 8A and 8B depict the time course of cleavage for CFP-DEVDR-YFP plasmid. Time is relative to the first frame taken after 8 h of STS treatment. FIG. 8A shows the fluorescence intensity of cyan fluorescent protein (CFP) and yellow fluorescent protein (YFP) in the CFP channel, plotted against time. FIG. 8B shows the CFP to YFP intensity ratio, plotted against time. The percentage rise in the CFP/YFP intensity ratio was 47%. Rise in CFP/YFP intensity ratio is an indirect measure of caspase-3/7 activation.

Figure 9:
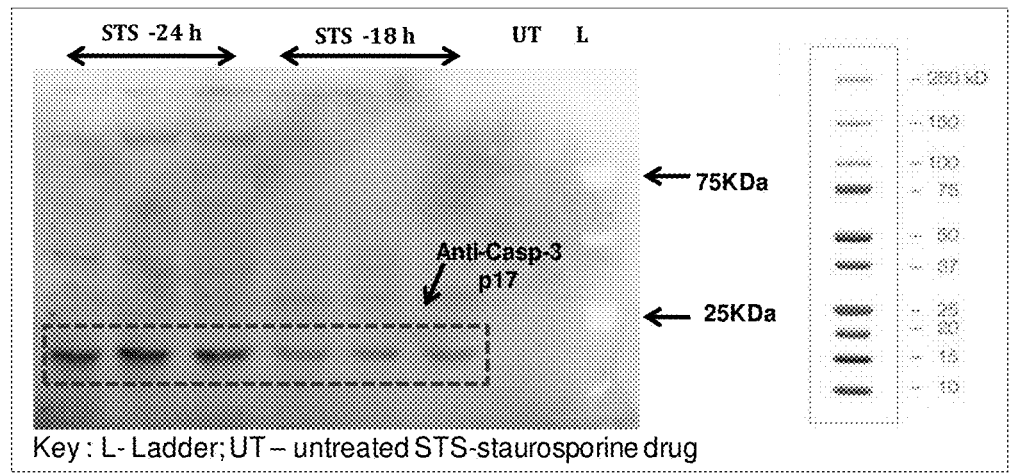

FIG. 9 depicts a western blot analysis of cleaved caspase-3 p17 fragment after 18 and 24 h of STS (1 μM) treatment in HeLa cells. Lysate loading was done in triplicates. Double headed arrow representing 3 lanes with the same sample.

Figures 10A, 10B:
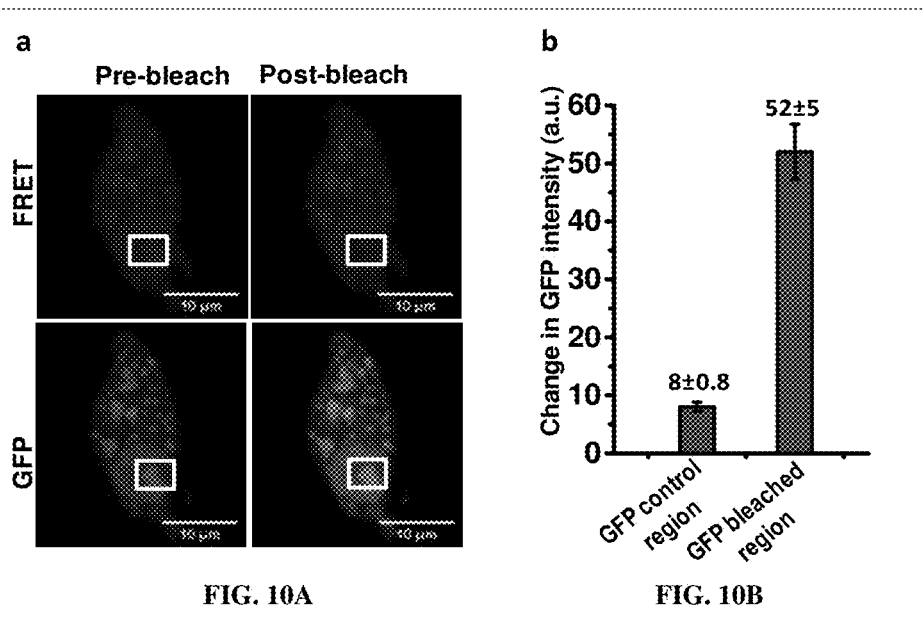

FIGS. 10A and 10B depict the specific detection of active caspase-3 in HeLa cells. Caspase-3 GFPspark (1 μg) transfected HeLa cells were treated with STS (1 μM) for 10 h. After 10 h of treatment, cells were labelled with probe 1 (1 μM) as described previously. As seen in FIG. 10A, images were obtained in GFP and FRET channels. FRET validation between GFPspark and rhodamine fluorophore using the acceptor photobleaching method. Images were taken under GFP and FRET channel pre- and post-rhodamine photobleaching in the ROI. As seen in FIG. 10B, the rise in GFP intensity in the ROI is 52±5 a.u. (n=15 cells), and the background is 8±1 a.u. The calculated FRET efficiency is 32±2%.

Figures 11A, 11B:
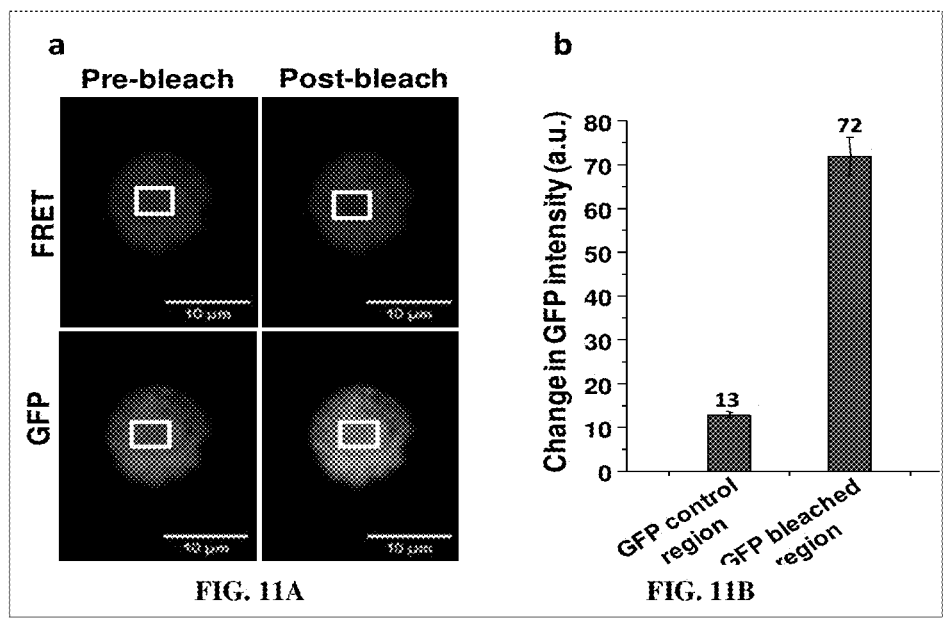

FIGS. 11A and 11B depict specific detection of active caspase-3 in HEK-293 cells. Caspase-3 GFPspark (1 μg) overexpressing HEK-293 cells were treated with STS (1 μM) for 10 h. After 10 h of STS treatment, cells were labelled with probe 1 (1 μM) as described previously. As seen in FIG. 11A, images were obtained in GFP and FRET channels. FRET validation between GFPspark and rhodamine fluorophore using the acceptor photobleaching method. I=intensity (a.u.), arbitrary units. Images were taken under GFP and FRET channel pre- and post-rhodamine photobleaching in the ROI. As seen in FIG. 11B, the rise in GFP intensity in the ROI is 72 a.u. and the background is 13 a.u. and the calculated FRET efficiency is 32.5±2%.

Figure 12:
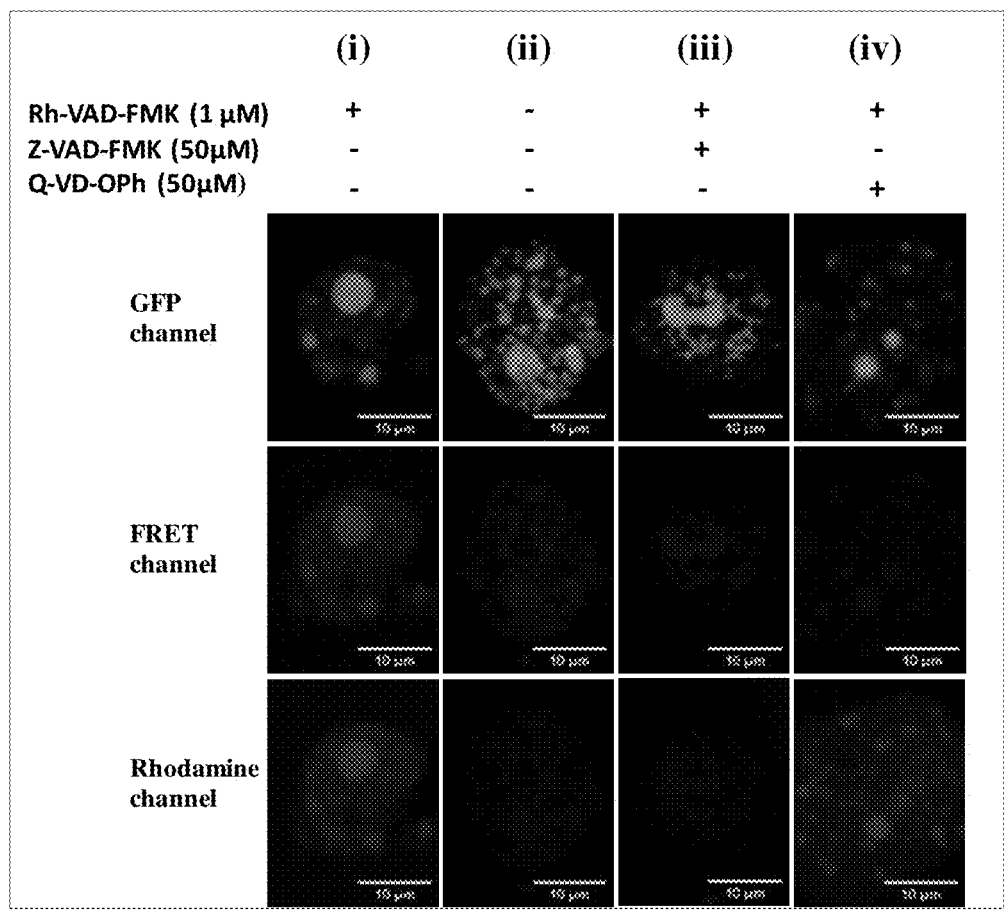

FIG. 12 depicts confocal images of MCF-7 cells in GFP, FRET and Rh channel. Caspase-3 GFPspark transfected MCF-7 cells were treated with STS for 4 h and labelled (a) with or (b) without probe 1. Cells were pre-treated with (c) Z-VAD-FMK (50 μM) and (d) Q-VD-OPh (50 μM) pan-caspase inhibitors 3 h before the probe labelling.

Figures 13A, 13B:
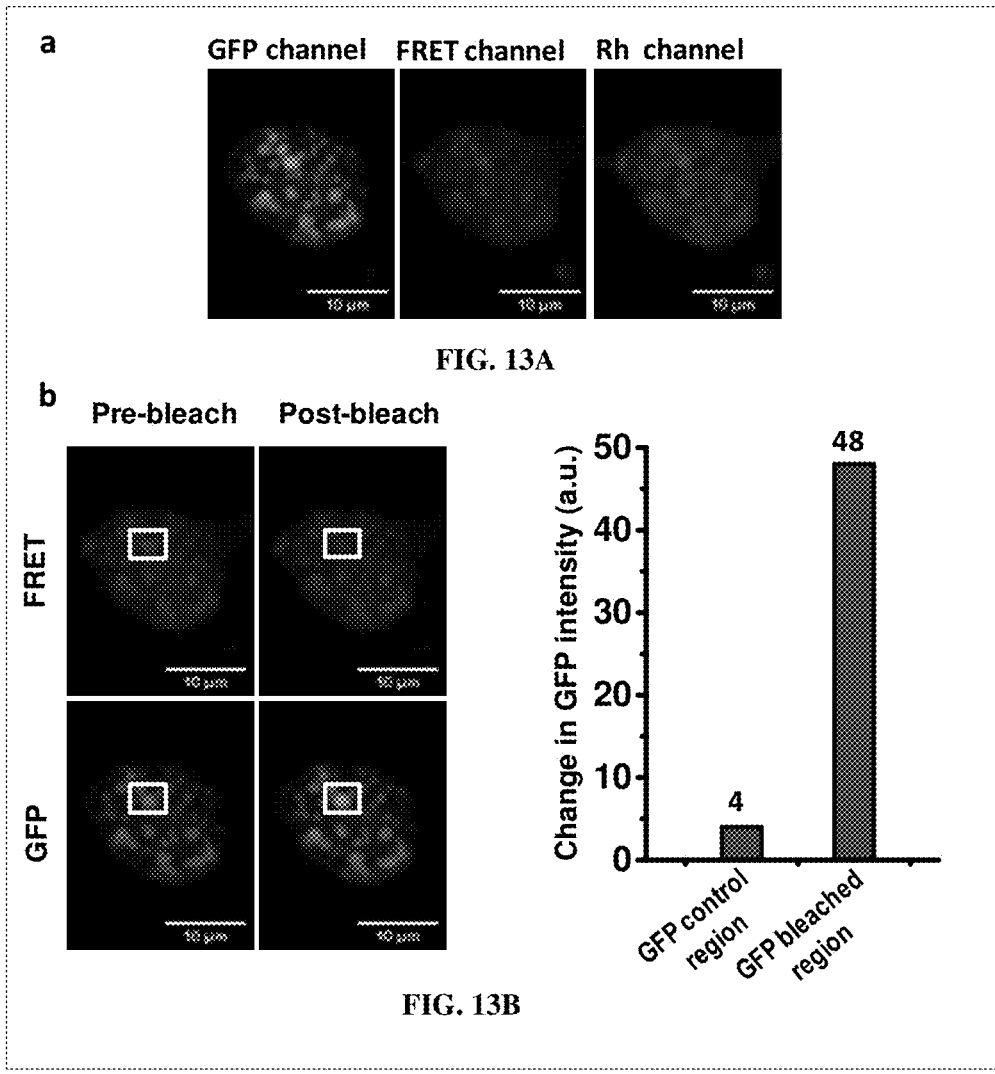

FIGS. 13A and 13B depict specific detection of caspase-7 GFPspark in MCF-7 cells. As seen in FIG. 13A, Casp-7 GFPspark (1 μg) transfected MCF-7 cells were treated with 1 μM of STS for 5 h and labelled with the probe 1 (1 μM). Cells were fixed and the fluorescence signal was collected in GFP, FRET and Rh channel. As seen in FIG. 13B, the acceptor photobleaching experiment was performed to confirm the FRET signal as described previously. Bar graph representing the rise in GFP intensity in ROI after rhodamine photobleaching was 89 a.u. as compared to the unbleached background, i.e., 9 a.u. FRET efficiency was calculated to be 32±2%.

Figure 14A:
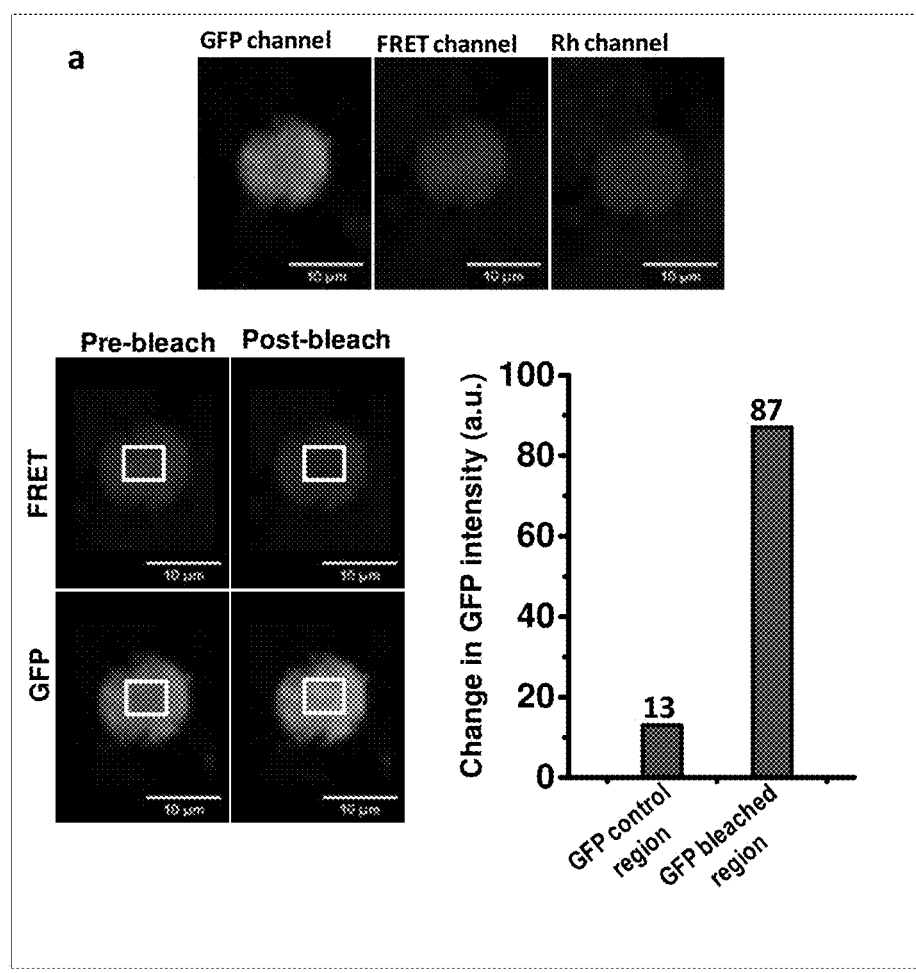
Figure 14B:
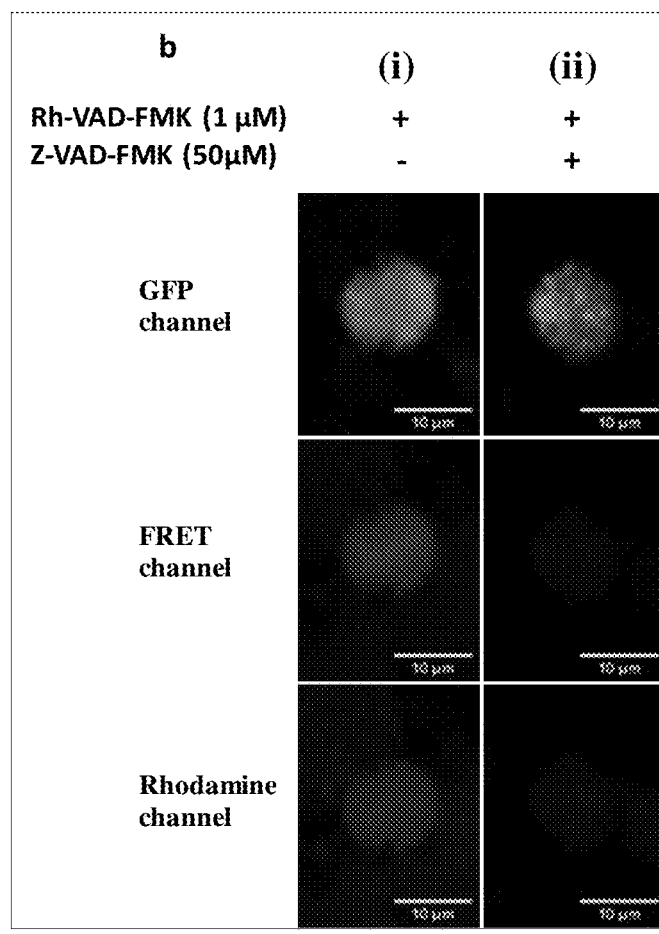

FIGS. 14A and 14B depict specific detection of caspase-7 GFPspark in HEK-293 cells. Caspase-7 GFPspark (1 μg) transfected HEK-293 cells were treated with STS (1 μM) for 10 h and labelled with the probe 1 (1 μM) for 2 h. As seen in FIG. 14A, cells were washed, fixed and the fluorescence signal was collected in GFP, FRET, and Rh channel. The acceptor photobleaching experiment was performed to confirm the FRET signal as described previously. Bar graph representing a rise in GFP intensity in ROI after rhodamine photobleaching was 87 a.u. as compared to the unbleached background, i.e., 13 a.u. FRET efficiency was calculated to be 33±2%. As seen in FIG. 14B, the fluorescence signal was collected in GFP, FRET and Rh channel in the (i) absence and (ii) presence of inhibitor Z-VAD-FMK (50 μM).

Figure 15:
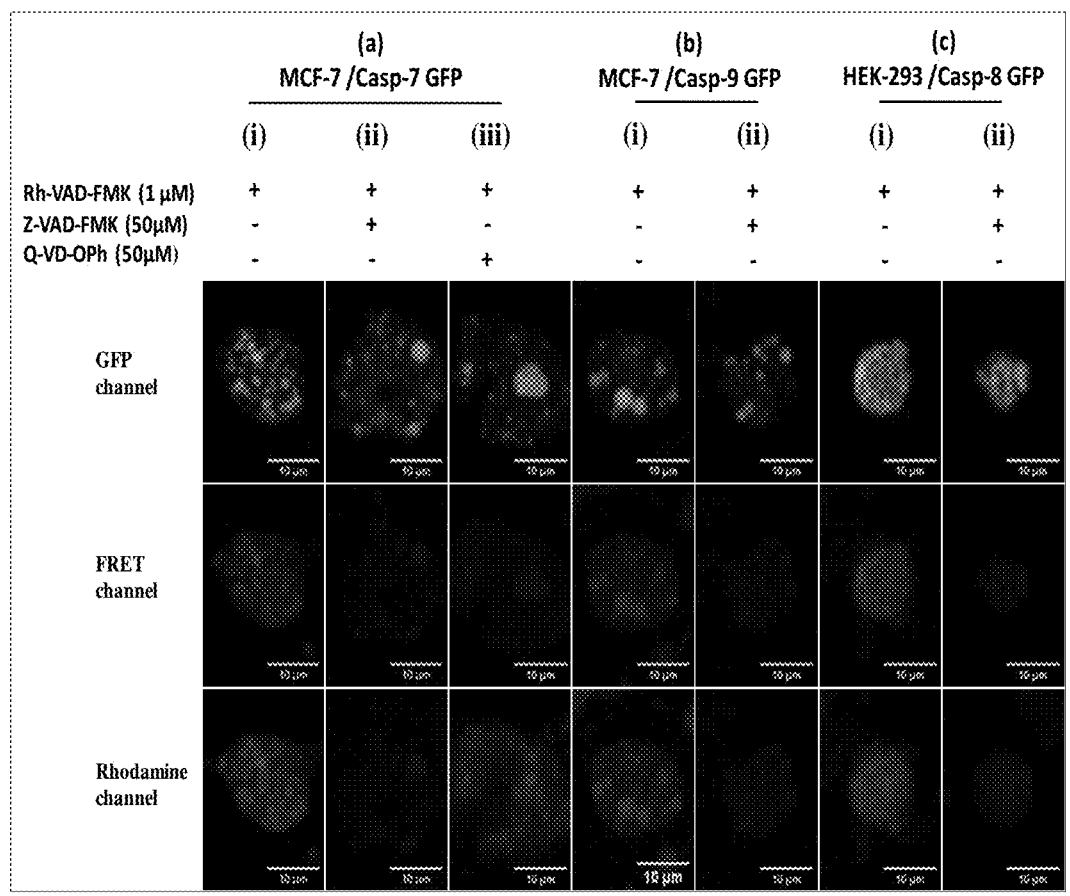

FIG. 15 depicts confocal images of MCF-7 cells in GFP, FRET and Rh channel Caspase-7 GFPspark transfected MCF-7 cells were treated with STS (1 μM) for 6 h and labelled (a) (i) with probe 1 (1 μM) probe. Cells were pre-treated with (a) (ii) Z-VAD-FMK (50 μM) or (a) (iii) Q-VD-OPh (50 μM) pan-caspase inhibitors 1 h before the probe labelling. Caspase-9 GFPspark transfected MCF-7 cells were treated with STS (1 μM) for 4 h and labelled (b) (i) with probe 1 (1 μM) probe. Cells were pre-treated with (b) (ii) Z-VAD-FMK (50 μM) 1 h before probe labelling. Caspase-8 GFPspark overexpressing HEK-293 cells were treated with TRAIL (1 μg/ml) for 5 h and labelled (c) (i) with the probe 1. Cells were pre-treated with (c) (ii) Z-VAD-FMK (50 μM) 1 h before probe labelling.

Figure 16:
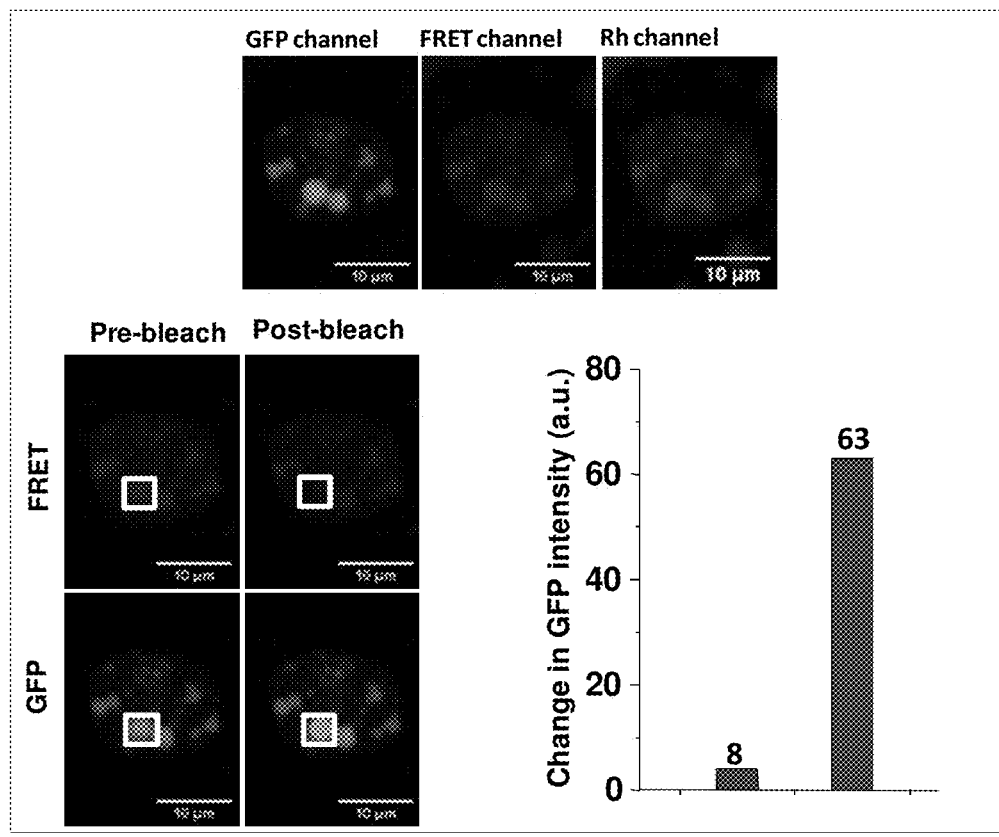

FIG. 16 depicts specific detection of caspase-9 GFPspark in MCF-7 cells. Casp-9 GFPspark (1 μg) transfected MCF-7 cells were treated with STS (1 μM) for 4 h and labelled with the probe 1 (1 μM). Cells were fixed and the fluorescence signal was collected in GFP, FRET and Rh channels. The acceptor photobleaching experiment was carried out to confirm the FRET signal as described previously. Bar graph representing a rise in GFP intensity in ROI after rhodamine photobleaching was 63 a.u. as compared to the unbleached background, i.e., 8 a.u. FRET efficiency was calculated to be 30±1%.

Figure 17A:
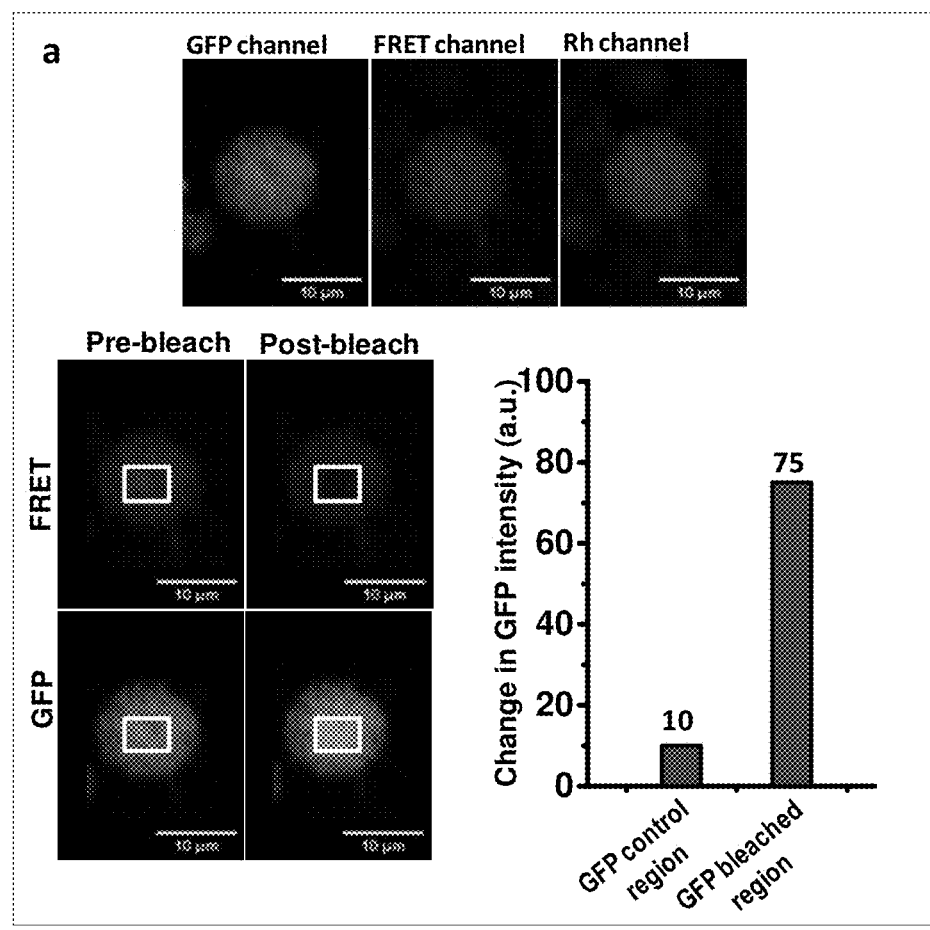
Figure 17B:
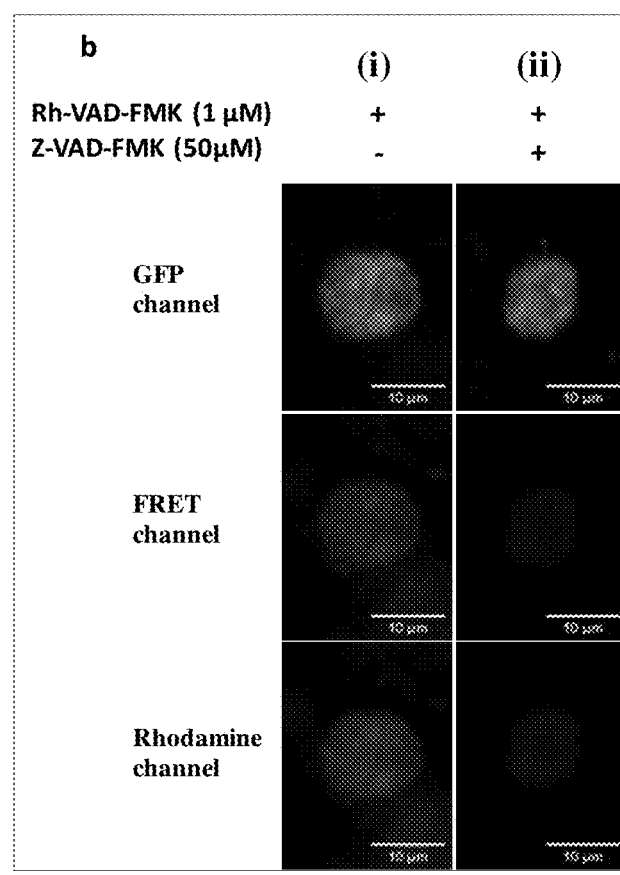

FIGS. 17A and 17B depict specific detection of caspase-9 GFPspark in HEK-293 cells. Casp-9 GFPspark (1 μg) transfected HEK-293 cells were treated with STS (1 μM) for 4 h and labelled with the probe 1 (1 μM) for 2 h. As seen in FIG. 17A, cells were washed, fixed and the fluorescence signal was collected in GFP, FRET, and Rh channel. The acceptor photobleaching was performed to confirm the FRET signal as described previously. The bar graph representing the rise in GFP intensity in ROI after rhodamine photobleaching was 75 a.u. as compared to the unbleached background, i.e., 10 a.u. FRET efficiency was calculated to be 35±2%. As seen in FIG. 17B, the fluorescence signal was collected in GFPspark, FRET and Rh channel in the (i) absence and (ii) presence of inhibitor Z-VAD-FMK (50 μM).

Figure 18:
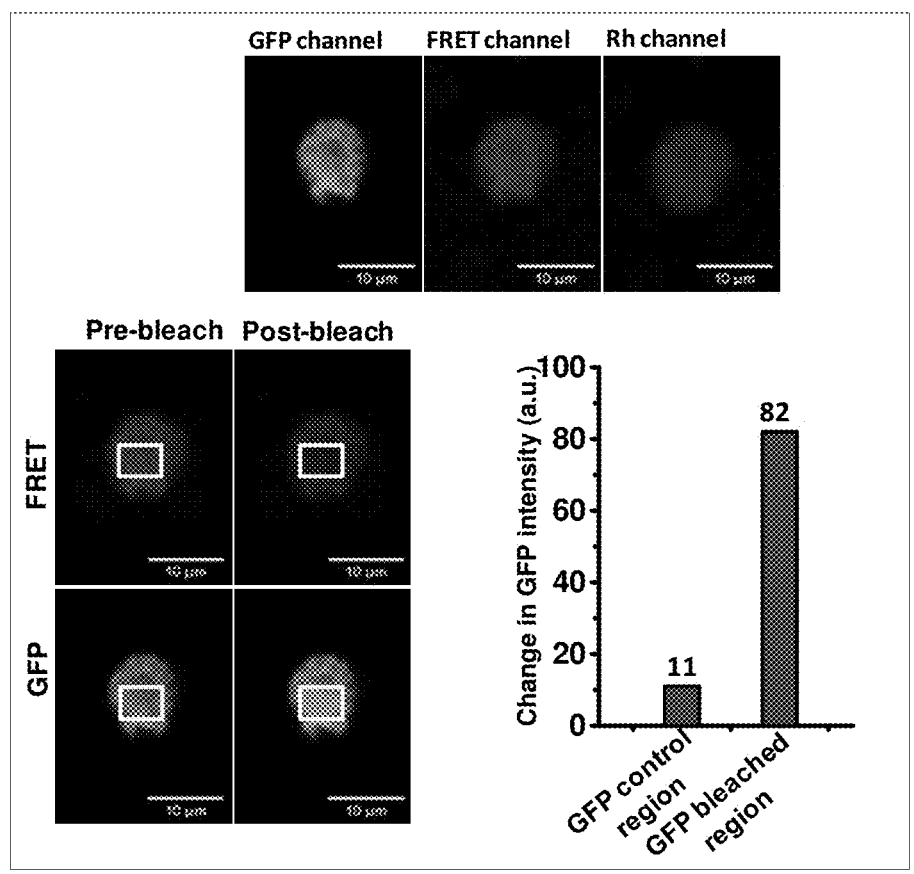

FIG. 18 depicts specific detection of caspase-8 GFPspark in HEK-293 cells. Casp-8 GFPspark (1 μg) transfected HEK-293 cells were treated with TRAIL (1 mg/ml) for 6 h and labelled with the probe 1 (1 μM) for 2 h. Cells were washed, fixed and the fluorescence signal was collected in GFP, FRET and Rh channels. The acceptor photobleaching experiment was performed to confirm the FRET signal as described previously. The bar graph representing a rise in GFP intensity in ROI after rhodamine photobleaching was 82 a.u. as compared to the unbleached background, i.e., 11 a.u. The FRET efficiency was calculated to be 31±1%.

Figure 19:
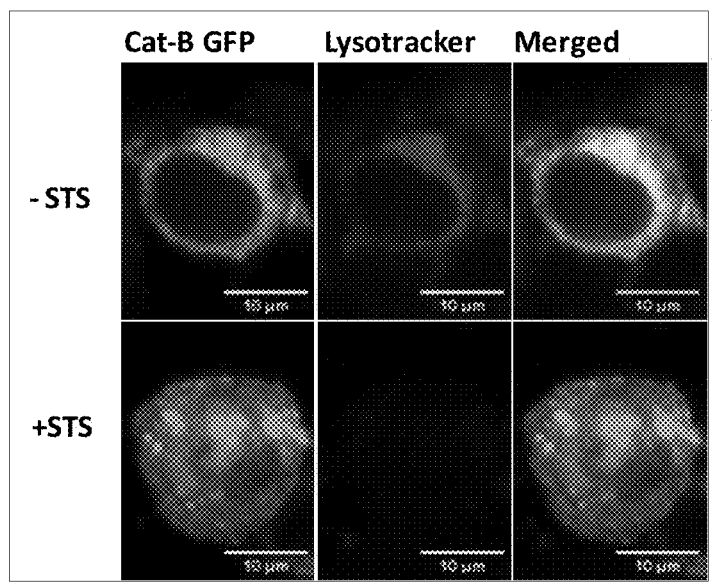

FIG. 19 depicts co-localization of cathepsin B GFPspark and LysoTracker. Cathepsin B GFPspark (1 µg) plasmid transfected in HEK-293 cells and then labelled with LysoTracker (50 nM) for 1 h and treated with STS (1 µM) for 1 h. Images under GFP and Red channel. GFP signal found to be co-localized with red fluorescence signal in the absence of STS and no co-localization was seen in the presence of STS.

Figure 20:
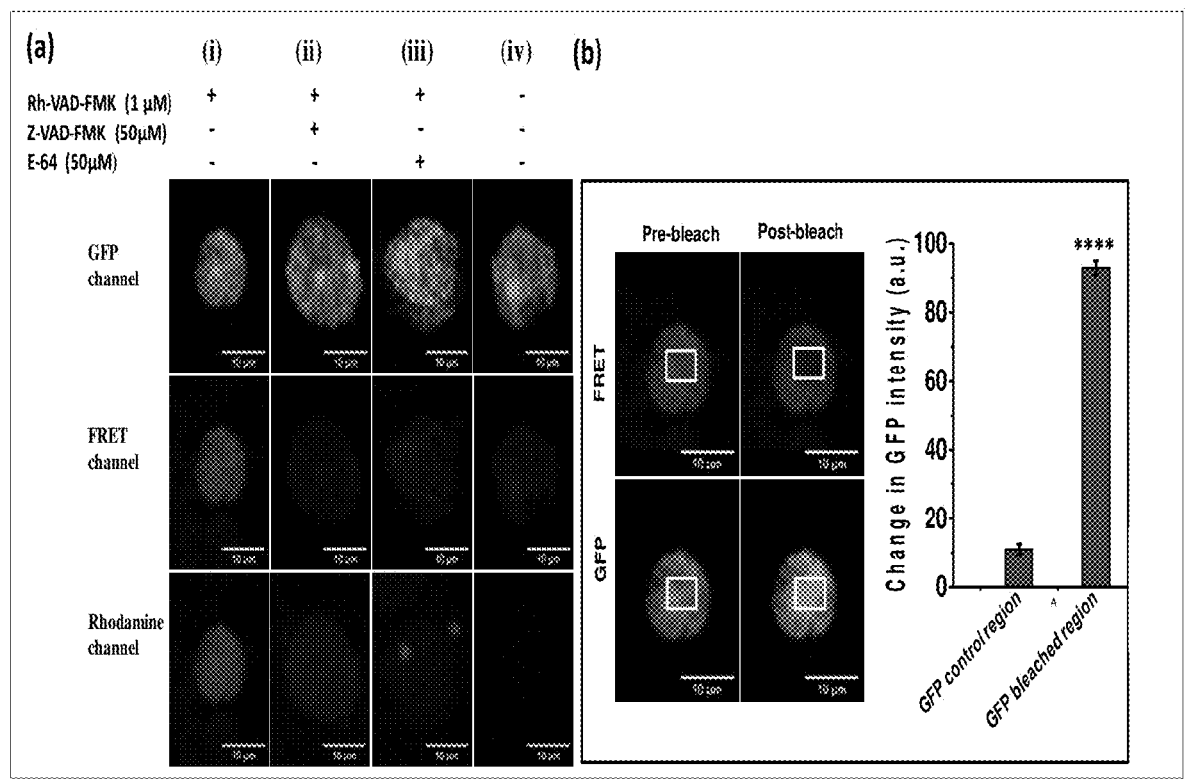

FIG. 20 depicts confocal images of HEK-293 cells in GFP, FRET and Rh channel Cathepsin B GFPspark transfected HEK-293 cells were treated with STS (1 µM) for 4 h and labelled (a) (i) with or (a) (iv) without probe 1. Cells were pre-treated with (a) (ii) Z-VAD-FMK (50 µM) or (a) (iii) E-64 (50 µM) inhibitor 1 h before the probe 1 labelling. (b) Quantification of the change in GFPS fluorescence intensity after rhodamine photobleaching in both unbleached control region and rhodamine bleached region (ROI), using acceptor photo-bleaching method. Error bar represents the s.e.m for n=10 cells (*P<0.00001). Scale bar, 10 µm. a.u., arbitrary units.

DETAILED DESCRIPTION OF THE INVENTION

The invention will now be described in detail in connection with certain preferred and optional embodiments, so that various aspects thereof may be more fully understood and appreciated.

The present invention provides an activity-based reporter gene technology (AbRGT) technology. The concept of AbRGT to detect the activity of an EoI (Enzyme of interest) in the present invention is schematically shown in FIG. 1.

In a preferred embodiment, the present invention provides a process for determining the activity of an enzyme in a cell by using AbRGT comprising;
  (a) preparing or obtaining a cell overexpressing the enzyme of interest (EoI) tagged to a reporter protein acting as a fluorescence donor with an inducing agent,
  (b) introducing an fABP comprising a warhead, a linker sequence, and a fluorescent acceptor moiety into the cell,
  (c) allowing the fABP (acceptor) to covalently modify the EoI tagged to a reporter protein (donor) resulting in the formation of an in-situ FRET pair, and
  (d) measuring the fluorescent read out.

Accordingly, the EoI with a FRP can be expressed in any cell line of interest. Upon the application of an appropriate stimulus, required for enzyme activation, a cell-permeable fABP with a fluorescent tag is added to the cell.

The selection of the fABP depends on the warhead and fluorescent tag. The warhead should be such that it reacts with the catalytic active-site of the enzyme and the fluorescent tag should make a FRET pair with enzyme tagged to the FRP. The FRET phenomenon occurs only if the distance between the FRP (fluorescence energy donor) tagged to the target EoI and the fluorescent tag of the fABP (fluorescence energy acceptor) is less than 10 nm. FRET is a highly distance dependent phenomenon; therefore labelling of other enzymes by fABP will not result in any FRET effect. Hence, according to the process of the present invention, the FRET signal that will be obtained will be highly specific to the target EoI.

In a preferred embodiment, the present invention provides a method for imaging and analyzing the activity of an enzyme comprising; (i) expressing a recombinant enzyme construct comprising a polypeptide chain tagged to a FRP donor moiety into a host cell; and (ii) subjecting the transfected host cell of step (i) to a stimulus followed by addition of fABP moiety containing acceptor fluorophore to the transfected host cell to form an in-situ FRET pair; wherein the donor and acceptor moieties exhibit FRET and the activity of the target EoI is determined.

Accordingly, in an embodiment, the present invention provides a process for monitoring and analyzing the activity of enzymes selected from the group of cysteine protease such as caspase-3, -7, -8 and -9 and cathepsin B in the apoptosis pathway.

In an embodiment, the present invention provides the FRP donor moiety, i.e., the FRP is selected from GFP (Green Fluorescent Protein) and it can be selected from its variants such as CFP (Cyan Fluorescent Protein)), YFP (Yellow Fluorescent Protein), BFP (Blue Fluorescent protein), RFP (Red Fluorescent Protein) and the like.

In another embodiment, the present invention provides the fluorescent acceptor moiety of fABP is selected from the group comprising sulpho-rhodamine and also be selected from whole range of dyes with an absorption range of (550-650 nm) such as alexafluor dyes, cyanine dyes, etc.

The cell lines are overexpressed with EoI tagged to the FRP plasmid construct of the present invention are selected from the group comprising HeLa, HEK-293 and MCF-7 cells.

In another preferred embodiment, the present invention provides a process for determining the activity of caspases and cathepsin B and in a cell by using AbRGT comprising;
  (a) preparing a cell overexpressing caspase tagged to a fluorescent donor moiety with an inducing agent, followed by
  (b) introducing an fABP comprising a warhead, a linker sequence, and a fluorescent acceptor moiety into the said cell,
  (c) allowing the fABP to modify the active caspase tagged to the reporter protein to result in an in-situ FRET pair, and
  (d) measuring the FRET read out.

The process above is also applied to determine the activity of cathepsin B during apoptosis.

In a further, embodiment, the present invention provides an fABP comprising;
  (a) a fluorophore selected from the group comprising fluoromethyl ketone (FMK), (acyloxy) methyl ketone (AOMK), E-64, and Q-VD-OPh.
  (b) a linker sequence selected from the group comprising VAD, DEVD, VD, and D
  (c) a fluorescent acceptor moiety selected from the group of dyes having absorption spectrum in the region ranging from 550-650 nm such as sulpho-rhodamine, alexa fluor and the like.

The linker sequence VAD is Valine-Alanine-Aspartate, DEVD is Aspartate-Glutamate-Valine-Aspartate, VD is Valine and Aspartate and D is Aspartate.

In accordance with the aforesaid embodiment, the present invention provides a process for determining the activity of caspases and cathepsin B. The cell line expressed with the recombinant enzyme construct comprising a caspase-3 enzyme linked to a FRP, i.e., GFPspark in a host cell were subjected to apoptosis through the addition of drug staurosporine. Upon such apoptotic stimuli, a cell-permeable fABP was added. The fABP reacts with a catalytic residue of "active" caspase-3-GFPspark fusion protein. Before labelling, excitation of GFPspark emits at 507 nm, however, after labelling, the fluorescence emission from GFPspark will be transferred to the fluorophore sulpho-rhodamine (tag of the fABP), resulting in quenching of GFPspark fluorescence with simultaneous excitation of the fluorophore of fABP probe. Excited GFPspark would now emit at longer wavelength resulting in the FRET effect. The FRET between GFPspark and rhodamine fluorophore was confirmed and ensured that the signal obtained in the FRET channel is indeed true FRET signal and specific to caspase-3 activation.

Further, the activity of caspase-7 in the apoptosis signalling pathway was also analyzed. MCF-7 cells expressing caspase-7 GFPspark (MCF-7/casp-7 GFPspark) were treated with STS for 6 h. After STS induction, cells were incubated with the probe 1 for an additional 2 h. Cells were washed, fixed and imaged under a confocal microscope. The fluorescence signal was captured in GFP, FRET and Rh channel. Casp-7 GFPspark transfected MCF-7 cells showed punctate pattern in GFP channel [FIG. 15a (i)] similar to caspase-3 GFPspark [FIG. 2b (i)]. Fluorescence signal in the FRET channel specified active caspase-7 and was validated using the acceptor photobleaching method. The calculated FRET efficiency is 32±2% [FIG. 13 (a and b)]. In yet another preferred embodiment, the present invention provides adduct comprising caspase-GFPspark enzyme binds to the sulpho-rhodamine-VAD-fluoromethyl ketone. The adduct gives a FRET readout which can be employed in determining drug candidates, i.e., inhibitors screening for caspases in the treatment of several diseases such as acute neurological diseases, Huntington disease, Parkinson diseases, and Alzheimer's disease.

In one embodiment, the present invention provides a recombinant enzyme construct comprising a polypeptide chain linked to a fluorescent donor moiety; wherein the enzyme construct is subjected to stimuli in a host cell followed by addition of a fluorescent moiety having acceptor activity, wherein the donor and acceptor moieties exhibit fluorescence resonance energy transfer (FRET).

In yet another preferred embodiment, the present invention provides a nucleotide construct comprising sequences encoding regulatory elements operably linked to a nucleotide sequence encoding the recombinant enzyme construct. Further, the nucleotide construct is inserted in a plasmid vector for expression in a host cell.

In one preferred embodiment, the present invention provides a kit for identifying novel drug targets, for screening the specific activation of an enzyme in a biochemical pathway, testing the drug efficacy and to study the dynamics of enzyme activation, the kit comprising;
(a) a plasmid encoding recombinant fusion protein construct comprising a polypeptide chain of the enzyme to be screened linked to a fluorescent reporter protein (FRP); and
(b) a fABP with a fluorescent acceptor moiety;
wherein the donor and acceptor moieties exhibit fluorescence resonance energy transfer (FRET).

In one more preferred embodiment, the present invention provides a kit for identifying novel drug targets, for screening the activation of cysteine proteases in apoptosis, testing the drug efficacy and to study the dynamics of enzyme activation in an apoptotic pathway by using AbRGT, the kit comprising;
(a) a plasmid encoding recombinant fusion protein construct comprising a polypeptide chain of an enzyme selected from the cysteine protease group such as caspases or cathepsin to be screened linked GFP; and
(b) sulpho-rhodamine-VAD-fluoromethyl ketone the fluorescent acceptor moiety; and
(c) a drug for inducing the cell to undergo apoptosis is staurosporine or TRAIL (TNF-α related tumor-inducing ligand);

wherein the donor and acceptor moieties exhibit fluorescence resonance energy transfer (FRET).

The following examples, which include preferred embodiments, will serve to illustrate the practice of this invention, it being understood that the particulars shown are by way of example and for the purpose of illustrative discussion of preferred embodiments of the invention.

EXAMPLES

Example 1: Methodology

Reagents. Q-VD-OPh inhibitor (SML0063), E-64 inhibitor (E3132) and staurosporine drug (S5921) were purchased from Sigma Aldrich. Z-VAD-FMK inhibitor (G7231) was obtained from Promega. Probe 1 (ab65616) and Probe 2 (ab65617) were procured from Abcam. TRAIL recombinant protein (RPA139Hu01) was obtained from Cloud Clone Corporation.

Cell culture methods. MCF-7, HEK-293, and HeLa cells were cultured in Dulbecco's modified Eagle's medium (DMEM) (Gibco) supplemented with 10% fetal bovine serum (FBS) (Gibco), 100 mg/ml penicillin and 100 mg/ml streptomycin (Gibco). Cells were maintained at a density of $1\times10^6$ cells in T25 plate in a humidified atmosphere of 5% CO2 at 37° C.

Plasmids and transient transfection: GFPspark tagged plasmids; caspase-3 GFPspark tag (Cat: HG10050-ACG), caspase-7 GFPspark tag (HG10049-ACG), caspase-8 GFPspark (HG10078-ACG), caspase-9 GFPspark (HG11151-ACG) and cathepsin B GFPspark (HG10483-ACG) were procured from Sino Biological. For transfection, cells were seeded in a 6-well plate at a density of 0.4 million cells/well. At 60-70% confluency, cells were transiently transfected for 24 h at 37° C. with 1 µg of the GFPspark tagged plasmid DNA construct mixed with 5 µL of Lipofectamine 2000 (Invitrogen) according to the manufacturer's instructions. 24 h post-transfection, cells were visualized under the GFP filter for GFPspark expression under fluorescence microscope at 10× magnification.

Labelling of active caspases in apoptotic cells with FABP: After 24 h of transfection, cells were treated with STS (1 µM) drug or TRAIL (1 µg/ml) for apoptotic induction and incubated for 2, 4, 6 and 8 h at 37° C. in a humidified atmosphere of 5% CO2/95% air. Cells were gently scraped off from the surface at the end of apoptotic induction and centrifuged at 3000 rpm for 5 min. The cell pellet was resuspended in 300 µL of fresh DMEM containing 1 µM of probe for probe 2 and incubated for additional 2 h at 37° C. in a humidified atmosphere of 5% CO2. Cells were again centrifuged at 3000 rpm for 5 mins, and the supernatant was decanted. Cells were washed with 1×PBS, thrice finally resuspended in 20 µL of 1×PBS. The cell suspension was put on a slide, and a coverslip was placed over it. It was left for air drying. Slides were then imaged for GFP, FRET and rhodamine fluorescence signals under confocal microscopy.

Inhibitor assay: Cells were pre-treated with 50 µM of Z-VAD-FMK or Q-VD-OPh or E-64 inhibitor 1 h before probe 1 labelling and incubated for 1 h at 37° C. in a humidified atmosphere of 5% CO2. Cells were gently scraped off from the surface at the end of inhibitor treatment and centrifuged at 3000 rpm for 5 min Cells were then labelled with the probe 1 as described in the previous section.

Fluorescence imaging studies, FRET procedure: Images were collected on Zeiss LSM710 confocal microscope with 25 mW argon laser using Zen10 software. The laser was tuned to lines at 488 nm (excitation laser for GFPspark) and 561 nm (excitation laser for rhodamine) Cells were examined with a 40× 1.3 NA Zeiss oil immersion objective and 2.4× zoom. Images were collected in the three channels; GFP channel, argon laser tuned at 488 nm with 2% laser intensity and fluorescence emission was collected in emission range of 490-550 nm; rhodamine channel, argon laser tuned to 561 nm laser with 2% laser intensity and fluorescence emission was collected in range 550-650 nm and FRET channel with excitation laser of GFPSPARK channel and emission range of rhodamine channel. Images were captured and processed using Image J software.

Acceptor photobleaching method for FRET efficiency calculation: We used the acceptor photobleaching method to confirm FRET occurrence and also to calculate FRET efficiency. In this method, if FRET is occurring, donor intensity (GFPspark) rises after acceptor (rhodamine) photobleaching (Bastiaens et al., Proc. Natl. Acad. Sci., 1995). Cells were bleached for rhodamine fluorescence signals in the FRET channel at the region of interest (ROI), the area under the white box, using with 100% intensity (561 nm) for 200 iterations. Fluorescence intensities pre- and post-bleaching of rhodamine were determined, and change in GFP intensity after pre- and post-bleach was calculated. FRET efficiency was calculated using the equation mentioned below, (Bastiaens et al., Proc. Natl. Acad. Sci., 1995)—where (D) is the donor intensity.

$$\text{FRET efficiency} = \frac{(D)_{post\text{-}bleach} - (D)_{pre\text{-}bleach}}{(D)_{post\text{-}bleach}}$$

Example 2: Development of AbRGT Using Caspase-3 as the Target Enzyme

To establish AbRGT, the specific activation of caspase-3 GFPspark was monitored, in the apoptosis signalling pathway, using fABP, Rhodamine-VAD-fluoromethyl ketone (Rh-VAD-FMK) probe (probe 1) (Micale et al., JACS, 2004) [FIG. 2(a)] in MCF-7 cells. Here, rhodamine is the fluorescent tag, VAD is the peptide recognition sequence for caspases and FMK is the reactive warhead for targeting pan-caspases. Before monitoring the specific caspase-3 activation in the native cellular environment, the active-site labelling of probe 1 to the caspase-3 enzyme in in vitro conditions was first validated. The recombinant human caspase-3 His tagged enzyme (rcaspase-3) was expressed and purified using Ni-NTA column chromatography (Stennicke et al., Methods, 1999). The expression was confirmed by sodium dodecyl sulphate-polyacrylamide gel electrophoresis (SDS-PAGE) and matrix-assisted laser desorption/ionization-time of flight (MALDI-ToF) analysis [FIG. 3 (a & b)]. Now, to verify that the fABP, probe 1, effectively binds rcaspase-3 with good potency and selectivity, concentration dependent labelling of rcaspase-3 in the presence of different probe 1 concentrations (100, 500 and 2000 nM) was performed. The labelled enzyme samples were then separated on a 12% SDS-PAGE gel and were visualized using an in-gel fluorescence scanner.

Probe 1 effectively labelled rcaspase-3 at concentrations as low as 100 nM. As expected, the intensity for the caspase-3 p17 band increased with higher concentrations of the probe 1 [(FIG. 4 (a & b)]. Thermal denaturation of rcaspase-3 before labelling with probe 1 completely abolished the fluorescence signal, confirming that the reaction was driven through a specific mechanism between the enzyme active-site and the probe 1 warhead [FIG. 4(c)].

Having demonstrated that the probe 1 binds effectively to active caspase-3, AbRGT was applied to detect the specific activity of caspase-3 in native cellular environment using probe 1. MCF-7 cells were chosen because it lacks endogenous caspase-3. Plasmid encoding caspase-3 enzyme tagged to GFPspark FRP was transfected in MCF-7 cells for 24 h using reported protocol. MCF-7 cells expressing GFPspark (FRET donor)-caspase-3 fusion enzyme were treated with 1 µM STS, a protein kinase inhibitor, or TNF-α related tumor-inducing ligand (TRAIL) (1 µg/ml) for an apoptosis-induction. After 2, 4, 6 and 8 h of STS induction, cells were incubated with 1 µM probe 1 (FRET acceptor) for an additional 2 h. After 2 h of probe incubation, cells were washed with 1×PBS, fixed and imaged under a confocal microscope. Probe 1 as fABP was chosen because it has been previously shown that this probe 1 binds to caspase-3 with low selectivity and moderate affinity. Hence, it serves as a great probe to validate the present technology i.e. extensive probe engineering is not required. Also, the fluorophore (rhodamine derivative) attached to fABP can act as an excellent FRET acceptor because its absorption spectrum overlaps well with the emission spectrum of GFPspark, which is one of the prerequisites for the efficient FRET processes. To monitor the specific caspase-3 activation, the fluorescence signal was collected in three different channels; GFP (direct excitation and emission of GFP), FRET (direct excitation of GFP and indirect emission from rhodamine) and rhodamine (Rh) channel (direct excitation and emission of rhodamine). Caspase-3 GFPspark transfected cells showed distinct punctuate pattern in GFP, FRET and Rh channel in both [FIG. 2b (i)] STS and [FIG. 2b (ii)] TRAIL-treated cells after 4 h and 5 h of treatment respectively. The fluorescence signal in the FRET channel denotes the presence of active caspase-3. Diffused cytosolic distribution of GFPspark signal was observed in STS/TRAIL untreated control cells (data not shown) as pro-caspase-3 localization is known to be cytosolic (Zhivotovsky et al., Cell Death and Differentiation, 1999). Fluorescence signal obtained in Rh channel in untransfected MCF-7 cells [FIG. 2b (iii)], depicts probe 1 labelling of potential off-target enzymes (cathepsin B, legumain, other caspase enzymes, etc.).

To rule out that the obtained FRET signal in [FIG. 2b (i)] is not because of random physical interaction between GFPspark and rhodamine dye, MCF-7 cells were transfected with a plasmid encoding for enhanced green fluorescent protein (EGFP). EGFP transfected MCF-7 cells were treated with STS (1 µM) for 4 h, labelled with the probe 1. EGFP expression was observed in the GFP channel; no fluorescence signal was observed in the FRET channel as expected however distinct punctate labelling pattern was spotted in Rh channel depicts off-target labelling of other cysteine protease by probe '1 [FIG. 2b (iv)]. No labelling in the Rh channel was seen in STS/TRAIL untreated cells [FIG. 2b (v)]. In-gel fluorescence assay was also performed to validate the multiple off-targets labelling of probe 1 which has also been shown in the previous reports. Jurkat cell lysate (2 µg/µL) was incubated with 1 µM of probe 1 which showed multiple bands on SDS-PAGE gel upon rhodamine excitation at 561 nm laser [FIG. 5]. The present invention clearly demonstrates the off-target labelling of the probe 1. In order to further prove that the observed fluorescence signal in the FRET channel manifests exclusive detection of caspase-3 GFPspark and to rule out that the obtained signal is because of direct excitation of probe 1 (rhodamine dye) during FRET experiments, acceptor photo-bleaching studies were performed. Images in GFPspark and FRET channels were taken pre- and post-bleaching [FIG. 2(c)]. After rhodamine photo-bleaching with 561 nm laser with 100% intensity, the rise in GFP signal in ROI was observed. Quantification of GFPspark intensity pre- and post-rhodamine bleaching revealed a significant rise in GFPspark intensity in the rhodamine bleached region as compared to the unbleached region [FIG. 2(d)], confirming the in-situ occurrence of FRET pair and very specific detection of the target enzyme, i.e., caspase-3. The rise in GFP intensity after rhodamine photo-bleaching in the ROI is 58±3 a.u. However, the change in GFPspark intensity in the unbleached region was 6±1 a.u (P*≤0.00001) insignificant as compared to the bleached region. The calculated FRET efficiency for (n=15 cells) is 35±1%. Similar results were obtained for other time points i.e. 2, 6 and 8 h of STS treatment [FIG. 6 (a & b)]. Time-dependent imaging studies revealed huge cell to cell variability on the onset of programmed cell death and this observation is similar results obtained by other scientists. Caspase-3 activation was also monitored using probe 2 as fABP which is different from probe 1 in terms of peptide recognition sequence; DEVD in exchange for VAD as DEVD peptide sequence is more specific for caspases as compared to VAD. Probe 2 yielded a similar pattern of fluorescence signal in GFPspark, FRET and Rh channel as that of probe 1 [FIG. 7(a)]. The calculated FRET efficiency was 35% [FIG. 7(b)]. The present process was also validated by examining caspase-3 GFPspark activation in cell lines other than MCF-7 i.e. HeLa and HEK-293 cell line. It was initiated by first performing the substrate-based reporter assay, and single cell FRET analyses were performed to monitor the dynamics of activation of caspase cleaving the DEVD substrate. Live cell imaging studies revealed that caspase-3/7 activation occurs between 10-12 h after STS (1 µM) treatment [FIG. 8 (a & b)]. To confirm the reported results, the cleaved caspase-3 p17 fragment in immunoblotting was also detected by using active caspase-3 p17 antibody after 12 h of STS (1 µM) treatment [FIG. 9]. Based on the activation time window which is 10-12 h for caspase-3/7 AbRGT was performed for detecting specific activation of caspase-3 in HeLa cells. FRET signal was observed after 10 h of STS treatment indicating specific caspase-3 activation. Acceptor photo-bleaching method was done to confirm the FRET signal, and the calculated FRET efficiency was 32±2% [FIG. 10 (a & b)]. Similarly, in HEK-293 cells FRET signal was observed at 10 h of STS (1 µM) treatment and the calculated FRET efficiency is 33±2% [FIG. 11 (a & b)].

Example 3: Utilization of AbRGT for Inhibitors Screening

Over-activation of caspase-3 leads to several diseases such as acute neurological diseases, Huntington disease, Parkinson disease, and Alzheimer's disease. The inhibitors which are capable of blocking caspase-3 activity would be potential drug candidates. The development of fluorescence-based imaging method for the exclusive detection of "active enzymes" in complex in vivo conditions would be highly beneficial for the screening purpose. In order to show that the present method can be employed for drug screening studies, a proof-of-concept inhibitor screening experiment was performed.

For this reason, Z-VAD-FMK and Q-VD-OPh as pan-caspase inhibitors were selected for the present invention. FRET imaging studies were carried out in the [FIG. 12 (i)] absence and [FIG. 12 (iii)] presence of Z-VAD-FMK and also in the absence of probe 1 [FIG. 12 (ii)] As expected, Z-VAD-FMK (50 µM) completely abolished the in situ FRET effect and hence there was no fluorescence signal in the FRET channel as Z-VAD-FMK labelled all the activated caspase-3 GFPspark through the same mechanism as fABP (Rh-VAD-FMK) probe. However, in the presence of Q-VD-OPh (50 µM) inhibitor, FRET signal was indeed abolished, but distinct punctate labelling was detected in the Rh channel [FIG. 12 (iv)]. The fluorescence signal in the GFPspark channel did not overlap with the Rh channel indicating the off-target labelling of probe 1 to enzymes other than caspases.

Example 4: Determining the Specific Activation of Other Executioner and Initiator Caspases After validating the present technology by demonstrating its application in studying specific activation of caspase-3 GFPspark and in screening inhibitors, the present AbRGT approach was validated with an another executioner caspases, caspase-7. To monitor the specific activation of caspase-7 in the apoptosis signalling pathway, caspase-7 GFPspark plasmid was transfected in MCF-7 cells for 24 h. MCF-7 cells expressing caspase-7 GFPspark (MCF-7/casp-7 GFPspark were treated with 1 µM STS for 6 h. After 6 h of STS induction, cells were incubated with 1 µM probe 1 for an additional 2 h. Cells were washed with 1×PBS thrice, fixed and imaged under confocal microscope. The fluorescence signal was captured in GFP, FRET and Rh channel Casp-7 GFPspark transfected MCF-7 cells showed punctate pattern in GFP channel [FIG. 15a (i)] similar to caspase-3 GFPspark [FIG. 2b (i)]. Fluorescence signal in the FRET channel manifests the presence of active caspase-7 and was validated using the acceptor photobleaching method. The calculated FRET efficiency was 32±2% [FIG. 13 (a & b)]. The fluorescence signal in the Rh channel depicts the labelling of other cysteine protease including endogenous caspase-7. Pre-treatment of the cells with Z-VAD-FMK (50 µM) completely abolished the fluorescence signal in the FRET and Rh channel [FIG. 15a (ii)]. However, in the presence of Q-VD-OPh (50 µM) inhibitor, FRET signal was abolished as expected, but significant punctate labelling was seen in Rh channel [FIG. 15a (iii)] indicates the evidence of cross-labelling of the Probe 1. Similarly, in HEK-293 cells FRET signal was observed at 10 h of STS (1 µM) treatment and was abolished on pre-treatment with Z-VAD-FMK inhibitor (50 µM). The calculated FRET efficiency is 33±2% [FIG. 14(a & b)].

After establishing AbRGT in the context of executioner caspases, the focus was shifted towards initiator caspases. The present technology was further validated by monitoring the specific activation of initiator caspases (caspase-8 and -9). A similar procedure was followed for active enzyme determination as that of executioner caspase-3 and -7. Caspase-9 GFPspark plasmid was transfected in MCF-7 cells for 24 h, transfected cells were treated with STS (1 µM) for 4 h and labelled with the probe 1 for additional 2 h, and the fluorescence signal was collected in GFP, FRET and Rh channel [FIG. 15b (i)]. The signal in the FRET channel signifies exclusive activation of caspase-9 GFPspark. The calculated FRET efficiency was 30±1% [FIG. 16]. The addition of the Z-VAD-FMK (50 µM) inhibitor completely abolished the signal in FRET and Rh channel [FIG. 15b (ii)]. Similarly, in HEK-293 cells FRET signal was observed at 4 h of STS (1 µM) treatment and was abolished on pre-treatment with Z-VAD-FMK inhibitor (50 µM). The calculated FRET efficiency is 35±2% [FIG. 17 (a and b)].

To activate caspase-3, -7 and -9, STS (1 µM) was used as an apoptosis inducer which triggers cell death via intrinsic mechanism (Bertrand et al., Experimental Cell Research, (1994). To introduce another variable, TRAIL was used which induces apoptosis via extrinsic mechanism (Cell Press, 1995). To monitor the specific activation of caspase-8 GFPspark, HEK-293 cells were transfected with caspase-8 GFPspark plasmid for 24 h. Post-transfection cells were treated with TRAIL (1 µg/ml) for 6 h and labelled with the probe 1 for an additional 2 h. The florescence signal was collected in GFP, FRET and Rh channel [FIG. 4c (i)]. The calculated FRET efficiency in the FRET channel is 31±1% [FIG. 18]. The signal in FRET and Rh channel was abolished in the presence of Z-VAD-FMK inhibitor [FIG. 4c (ii)].

Example 5: Direct Imaging of Cathepsin B Activation in Apoptosis Pathway Using AbRGT Cathepsin B, a cysteine protease, plays a significant role in the necroptosis pathway, a programmed cell death pathway like apoptosis. In recent studies, the activity of cathepsin B in the cytosol of the apoptotic cells has been demonstrated via fABP technology (Pratt et al., Chem Biol., 2011). However, most of the studies were done in an invasive manner; therefore they do not provide the opportunity to study the spatiotemporal activation of cathepsin B in the apoptotic pathway. Using the present technology, the direct activation of cathepsin B GFPspark in apoptotic cells was imaged. The cathepsin B GFPspark was overexpressed in HEK-293 cells. Cells were then labelled with acidotropic lysosomal marker LysoTracker (50 nM). Cathepsin B GFPspark expression was found to co-localize with the LysoTracker as expected because the localization of cathepsin B is known to be lysosomal. The cells were induced to the apoptotic stimulus by treatment with STS (1 µM) for 4 h. Cathepsin B GFPspark expression did not co-localize with LysoTracker [FIG. 19]. Now, to directly image the cathepsin B activation in the apoptosis pathway, HEK-293 cells over-expressing cathepsin B GFPspark were treated with STS (1 µM) for 4 h and then labelled with probe 1 (1 µM) for 2 h. The fluorescence signal was captured in GFPspark, FRET and Rh channel [FIG. 20a (i)]. A diffused fluorescence signal was obtained in the FRET channel indicating the active cathepsin B GFPspark in apoptotic cells. As a control experiment, the cells were pre-treated with Z-VAD-FMK inhibitor (50 µM) 1 h before probe 1 labelling. After that, cells were labelled with the probe 1 for 2 h and washed extensively with 1×PBS, thrice. It was found that fluorescence signal was completely abolished in the FRET channel [FIG. 20a (ii)], however less intense fluorescence signal was still retained in the Rh channel FRET signal was also abolished in the cells that were pre-treated with E-64 (50 µM), a known epoxide based cysteine peptidase inhibitor. However, sharp, intense punctate labelling was observed in Rh channel [FIG. 20a (iii)], indicative of the cross-labelling of the probe 1. No fluorescence signal was seen in FRET and Rh that were neither pre-treated with any of the inhibitors nor labelled with the probe, as expected [FIG. 20a (iv)] These results demonstrated the direct activation of cathepsin B in the apoptotic pathway. The FRET efficiency of the fluorescence signal obtained in the FRET channel was also calculated using the acceptor photobleaching method [FIG. 20b] The FRET efficiency is 37±1%, for (n=10) cells.

Advantages of the Invention

The present technology can be employed in high-throughput studies for identifying novel drug targets, to screen the activation of an enzyme in a biochemical pathway, testing the drug efficacy and to study the dynamics of enzyme activation as it does not involve any post-processing of cell or tissue lysates.

The present invention measures the activity of target enzymes in apoptotic cells with accurate specificity to monitor the function of a target enzyme in a complex cellular environment in real time.

The present invention can be adopted to monitor the activation of any enzyme in both disease/normal state of a live cell or animal.

This tool can be extended for in vivo imaging of live animal by using red fluorescent protein (RFP)-EoI as FRET donor and fABP with a near-infrared fluorophore as a FRET acceptor.

This method can be extemporized to create an in-situ BRET (bio-luminescence energy transfer) pair by tagging EoI to luciferase enzyme and labelling with fABP, which can accept energy released from the conversion of luciferin to oxy-luciferin. BRET approach offers an advantage of longitudinal in vivo imaging.

This technology can be used for profiling of enzyme inhibitors and hence serves its application in screening of drugs and other therapeutic purposes.

We claim:

1. A process for determining the activity of an enzyme of interest (EoI) in a cell by using activity-based reporter gene technology (AbRGT) comprising;
   (a) preparing a cell overexpressing the EoI tagged to a reporter protein acting as a fluorescence donor with an inducing agent,
   (b) introducing a fluorescently labelled activity-based probe (fABP) comprising a warhead, a linker sequence, and a fluorescent acceptor moiety into the cell,
   (c) allowing the fABP containing fluorescent acceptor to covalently modify the EoI tagged to reporter protein to form an in-situ fluorescence resonance energy transfer (FRET) pair, and
   (d) measuring a fluorescence signal from the FRET pair; wherein the fABP is rhodamine dye-DEVD-fluoromethyl ketone (FMK).

2. The process as claimed m claim 1, wherein the enzyme of interest is a cysteine protease.

3. The process as claimed in claim 2, wherein the cysteine protease is selected from the group consisting of caspase-3, caspase-7, caspase-8, caspase-9 and cathepsin B.

4. The process as claimed in claim 1, wherein the fluorescent donor is an exogenously expressed fluorescent reporter protein.

5. The process as claimed in claim 4, wherein the exogenously expressed fluorescent reporter protein is selected from the group consisting of GFP (Green Fluorescent protein), CFP (Cyan Fluorescent Protein), YFP (Yellow Fluorescent Protein), BFP (Blue Fluorescent protein), and RFP (Red Fluorescent Protein).

6. The process as claimed in claim 1, wherein the rhodamine dye is having an absorption spectrum in the region ranging from 550-650 nm.

7. The process as claimed in claim 6, wherein the rhodamine dye having an absorption spectrum in the region ranging from 550-650 nm is a sulpho-rhodamine dye.

8. A process for determining the activity of caspases involved in apoptosis in a cell by using activity-based reporter gene technology (AbRGT) comprising,
   (a) preparing a cell overexpressing caspase tagged to a fluorescent donor moiety with an inducing agent, (b) introducing a fluorescently labelled activity-based probe (fABP) comprising a warhead, a linker sequence, and a fluorescent acceptor moiety into the cell, (c) allowing the caspase tagged to a fluorescent donor moiety to bind to the fABP to Result in a fluorescence resonance energy transfer (FRET) signal, and (d) measuring the FRET signal; wherein the fABP is rhodamine dye-DEVD-fluoromethyl ketone (FMK).

9. The process as claimed in claim 8, wherein the fluorescent donor moiety is an exogenously expressed fluorescent reporter protein.

10. The process as claimed in claim 9, wherein the exogenously expressed fluorescent reporter protein is selected from the group consisting of GFP (Green Fluorescent protein), CFP (Cyan Fluorescent Protein), YFP (Yellow Fluorescent Protein), BFP (Blue Fluorescent protein), and RFP (Red Fluorescent Protein).

11. The process as claimed in claim 1, wherein the fABP is sulphorhodamine-DEVD-fluoromethyl ketone.

12. The process as claimed in claim 11, wherein the enzyme of interest is a caspase-GFP enzyme which binds to the sulpho-rhodamine-DEVD-fluoromethyl ketone.

13. The process as claimed in claim 8, wherein the caspase is induced through apoptotic stimuli by the addition of staurosporine or TRAIL.

* * * * *